(12) United States Patent
Mast et al.

(10) Patent No.: US 12,364,462 B2
(45) Date of Patent: Jul. 22, 2025

(54) ABLATION MONITORING AND CONTROL USING THREE-DIMENSIONAL ECHO DECORRELATION IMAGING

(71) Applicant: University of Cincinnati, Cincinnati, OH (US)

(72) Inventors: T. Douglas Mast, Cincinnati, OH (US); Peter D. Grimm, Cincinnati, OH (US); Elmira Ghahramani Zarajabad, New York, NY (US)

(73) Assignee: University of Cincinnati, Cincinnati, OH (US)

( * ) Notice: Subject to any disclaimer, the term of this patent is extended or adjusted under 35 U.S.C. 154(b) by 89 days.

(21) Appl. No.: 18/317,342

(22) Filed: May 15, 2023

(65) Prior Publication Data
US 2023/0363738 A1    Nov. 16, 2023

Related U.S. Application Data

(60) Provisional application No. 63/341,831, filed on May 13, 2022.

(51) Int. Cl.
*A61B 8/00*       (2006.01)

(52) U.S. Cl.
CPC .............. *A61B 8/469* (2013.01); *A61B 8/483* (2013.01); *A61B 8/5207* (2013.01); *A61B 8/5223* (2013.01)

(58) Field of Classification Search
CPC ....... A61B 8/469; A61B 8/483; A61B 8/5207; A61B 8/5223
See application file for complete search history.

(56) References Cited

U.S. PATENT DOCUMENTS

| | | | |
|---|---|---|---|
| 7,846,096 B2 | 12/2010 | Mast et al. | |
| 8,556,888 B2 | 10/2013 | Nields et al. | |
| 2004/0127791 A1 | 7/2004 | Mast et al. | |
| 2005/0240105 A1 | 10/2005 | Mast et al. | |
| 2015/0272653 A1* | 10/2015 | Brunke | G16H 50/30 606/27 |

FOREIGN PATENT DOCUMENTS

| | | | | |
|---|---|---|---|---|
| CN | 108553763 A | * | 9/2001 | ........... A61B 8/0833 |

OTHER PUBLICATIONS

Cox, Michael T., Mohamed A. Abbass, and T. Douglas Mast. "Numerical analysis of three-dimensional echo decorrelation imaging." The Journal of the Acoustical Society of America 147.6 (2020): EL478-EL483. (Year: 2020).*

(Continued)

*Primary Examiner* — Sean D Mattson
(74) *Attorney, Agent, or Firm* — Wood Herron & Evans LLP

(57) ABSTRACT

Systems, methods, and computer program products for monitoring and control of tissue ablation using three-dimensional echo decorrelation imaging. A first plurality of pulse-echo image volumes each including a region of interest are received from an ultrasound scanner. One or more pulse-echo image volume pairs are defined from the plurality of pulse-echo image volumes. Echo decorrelation image volumes are defined from the pulse-echo image volume pairs, and an amount of power provided to an ablation probe located in the region of interest is determined based on the echo decorrelation image volume.

18 Claims, 15 Drawing Sheets

(56) References Cited

OTHER PUBLICATIONS

Abbass, Mohamed A. Real-time control of ultrasound thermal ablation using echo decorrelation imaging feedback. Diss. Doctoral dissertation, University of Cincinnati]. OhioLINK Electronic Theses and Dissertations Center. http://rave.ohiolink.edu/etdc/view, 2018. (Year: 2018).*

Hooi, Fong Ming, et al. "Analysis of tissue changes, measurement system effects, and motion artifacts in echo decorrelation imaging." The Journal of the Acoustical Society of America 137.2 (2015): 585-597. (Year: 2015).*

Subramanian, Swetha, et al. "In vivo thermal ablation monitoring using ultrasound echo decorrelation imaging." Ultrasound in medicine & biology 40.1 (2014): 102-114. (Year: 2014).*

Elmira Ghahramani et al., Three-dimensional echo decorrelation imaging of percutaneous microwave ablation in liver tumors, The Journal of the Acoustical Society of America, vol. 150, Issue 4, Nov. 18, 2021.

Bahar Saremi et al., Motion-corrected echo decorrelation imaging for monitoring exvivo cardiac ablation, Abstract, The Journal of the Acoustical Society of America 151, A212, May 10, 2022.

Elmira Ghahrami Z. et al, In Vivo thermal ablation control using three-dimensional echo decorrelation imaging in swine liver, Abstract, The Journal of the Acoustical Society of America 152, A278, Nov. 29, 2022.

Peter D. Grimm Jr., Real-time control of radiofrequency thermal ablation using three-dimensional ultrasound echo decorrelation imaging feedbeck, Masters Thesis, University of Cincinnati, Jul. 18, 2022.

Elmira Ghahramani Z. et al., Control of radiofrequency ablation in ex vivo human liver tissue using 3D echo decorrelation imaging feedback, 2021 IEEE International Ultrasonics Symposium (IUS), Sep. 11-16, 2021.

E. Ghahramani Z. et al, Three-dimensional echo decorrelation monitoring of radiofrequency ablation in ex vivo bovine liver, The Journal of the Acoustical Society of America 151, pp. 3907-3918, Jun. 9, 2022.

Hamid R.S. Neshat et al, Development of a 3D ultrasound-guided system for thermal ablation of liver tumors, Proc. of SPIE Medical Imaging, Lake Buena Vista, Florida, Mar. 14, 2013.

Mohamed A. Abbass et al., In vivo ultrasound thermal ablation control using echo decorrelation imaging in rabbit liver and VX2 tumor. PLoS One 14(12): e0226001, Dec. 5, 2019.

Elmira Ghahrahmani Z. et al., Ex vivo thermal ablation monitoring using three-dimensional ultrasound echo decorrelation imaging, J. Acoust. Soc. Am. vol. 145, Issue 3 Supplement, 1862, Mar. 1, 2019.

Matthew A. Lewis et al., Thermometry and ablation monitoring with ultrasound, International Journal of Hyperthermia vol. 31, 2015—Issue 2, Mar. 10, 2015.

\* cited by examiner

ABLATION MONITORING AND CONTROL USING THREE-DIMENSIONAL ECHO DECORRELATION IMAGING

CROSS-REFERENCE TO RELATED APPLICATIONS

The present application claims the filing benefit of U.S. Provisional Application Ser. No. 63/341,831, filed May 13, 2022, the disclosure of which is incorporated by reference in its entirety.

GOVERNMENT RIGHTS

This invention was made with government support under grant R01 CA158439, awarded by the National Institutes of Health. The U.S. Government has certain rights in the invention.

BACKGROUND

Thermal ablation is the clinical standard treatment for early-stage primary and metastatic liver cancer in patients who are ineligible for hepatic resection. The principle of operation in all thermal ablation procedures is to apply a thermal dose to the afflicted tissue to raise its temperature above 60° C., thereby inducing coagulative necrosis within a targeted region. Thermal energy may be delivered via alternating electric current as in radiofrequency ablation (RFA), electromagnetic wave radiation as in microwave ablation (MWA), or acoustic waves as in high intensity focused ultrasound (HIFU) ablation. In cases where the tumor is greater than two centimeters in diameter, ablation has similar efficacy to hepatic resection. But in the general case, ablation has a higher recurrence rate, as well as the potential for additional complications from damage to surrounding healthy tissue.

To ensure full treatment, physicians are advised to ablate a margin of two to five millimeters around the tumor. This margin then serves as the clinical target for evaluation of treatment efficacy. Although a large margin can substantially decrease the odds of recurrence, large margins are also associated with an increased risk of serious complications. For cases where the tumor's position precludes hepatic resection, it is especially pertinent that tumors are accurately ablated, with minimal damage to surrounding tissue, while also ensuring full necrosis of the diseased tissue.

Thermal ablation procedures are considered a second-line method of treatment due to their comparatively poor performance relative to hepatic resection in both metastatic and primary cases of liver cancer. Despite being the first-line method of treatment, hepatic resection is only applicable in 20-30% of patients, necessitating the application of treatment methods with relatively poor performance, such as thermal ablation. The relatively poor performance of thermal ablation may be attributed to a lack of precise targeting of cancerous tissue relative to the precision of surgical resection. Inaccurate targeting has two potential adverse effects, namely cancer recurrence if the tissue is undertreated, and damage to vital, healthy tissue if the tumor is overtreated. Recurrence because of undertreatment occurs in 15-20% of patients, and thus requires additional rounds of therapy to assure long-term disease-free survival. Overtreatment can worsen clinical outcomes through damage to vital supportive tissue, such as the hepatic artery or portal vein.

In radiofrequency ablation, frictional heat is generated by the alternating electrical current passing through tissue and causing rapid oscillation of ions. The generated heat then transfers to areas of tissue that are not along the electrical path due to thermal conduction. Radiofrequency ablation is a common treatment for nonresectable liver tumors, including hepatocellular carcinoma and colorectal metastases, and may be the most widely used method of image-guided local thermal ablation for hepatocellular carcinoma up to 50 mm in diameter. Although radiofrequency ablation can provide survival rates comparable to surgical resection, the frequency of local tumor recurrence after radiofrequency ablation is often higher than surgery. Real-time monitoring of ablation progress may help to avoid incomplete ablation treatments and resulting local recurrence of tumors and is an active area of research.

Magnetic resonance imaging (MRI) has been used for monitoring thermal ablation by real-time magnetic resonance thermometry. However, this approach can be both costly and inconvenient. Another ablation monitoring method is computed tomography-guided radiofrequency ablation, which provides better edge detection of ablated lesions than magnetic resonance imaging, but also has downsides such as long procedure time, radiation exposure, potential contrast-induced nephropathy, and high cost.

Ultrasound guidance of radiofrequency ablation includes the advantages of lower cost, portability, and real-time operation. Pulse-echo ultrasound guidance methods for thermal ablation include conventional B-mode (brightness mode) imaging, contrast-enhanced B-mode imaging, echo energy-based methods such as integrated backscatter imaging, and cross correlation-based methods such as elastography, thermal strain imaging, and thermal expansion imaging. The latter methods quantify strain within pulse-echo scan lines caused by applied mechanical stress, temperature dependence of the speed of sound, and local expansion of tissue from heating and coagulation.

However, while thermal ablation is under way, pulse-echo ultrasound monitoring methods are limited by inconsistent, transient heat-induced changes in tissue reflectivity, pulse-echo signal decorrelation due to vapor bubble activity and tissue state changes, and complex dependence of tissue acoustic and viscoelastic properties on temperature. Moreover, because radiofrequency ablation and similar bulk thermal ablation methods treat large volumes of heterogeneous tumor tissue simultaneously, two-dimensional imaging is insufficient to monitor ablation progress. This issue may be even more significant when treating multiple neighboring tumors simultaneously.

Therefore, there is a need for systems, methods, and computer program products that improve the accuracy of thermal ablation procedures to reduce the incidence of complications arising from tumor overtreatment and undertreatment.

SUMMARY

In an embodiment of the invention, a method of controlling an ablation process is provided. The method includes receiving a first plurality of pulse-echo image volumes each including a region of interest, defining a first pulse-echo image volume pair that includes a first pulse-echo image volume of the plurality of pulse-echo image volumes and a second pulse-echo image volume of the plurality of pulse-echo image volumes, and generating an echo decorrelation image volume from the first pulse-echo image volume pair. The method further includes one or more of adjusting an amount of power provided to an ablation probe located in the region of interest based on the echo decorrelation image volume, adjusting an amount of time power is provided to the ablation probe located in the region of interest based on the echo decorrelation image volume, and/or displaying the echo decorrelation image volume from the first pulse-echo image volume pair.

In an aspect of the method, adjusting the amount of power provided to the ablation probe based on the echo decorrelation image volume may include deriving a control parameter from the echo decorrelation image volume, and adjusting the amount of power provided to the ablation probe based on the control parameter.

In another aspect of the method, adjusting the amount of power provided to the ablation probe based on the control parameter may include comparing the control parameter to a predetermined threshold, and reducing the amount of power provided to the ablation probe in response to the control parameter exceeding the predetermined threshold.

In another aspect of the method, each pulse-echo image volume may include a plurality of pulse-echo image voxels each having a position within the pulse-echo image volume, the echo decorrelation image volume may include a plurality of echo decorrelation image voxels each associated with a respective pulse-echo image voxel of the plurality of pulse-echo image voxels, and the control parameter may be a spatial mean of each echo decorrelation image voxel within the region of interest or a minimum echo decorrelation value of the echo decorrelation image voxels within the region of interest.

In another aspect of the method, deriving the control parameter from the echo decorrelation image volume may include compensating for an artifactual decorrelation component of the echo decorrelation image volume to generate a corrected echo decorrelation image volume, and deriving the control parameter from the corrected echo decorrelation image volume.

In another aspect of the method, each pulse-echo image volume may include a plurality of pulse-echo image voxels each having a position within the pulse-echo image volume, the echo decorrelation image volume may include a plurality of echo decorrelation image voxels each associated with a respective pulse-echo image voxel of the plurality of pulse-echo image voxels, and generating the corrected echo decorrelation image volume may include calculating a motion-induced decorrelation value produced by a movement in a reference region of interest. In this aspect of the method, for each echo decorrelation image voxel of the echo decorrelation image volume, the method may include subtracting the motion-induced decorrelation value from an echo decorrelation value of the echo decorrelation image voxel to define a difference value, and using the difference value define a corrected echo decorrelation value of a corrected echo decorrelation image voxel of the corrected echo decorrelation image volume.

In another aspect of the method, the method may further comprise, for each echo decorrelation image voxel of the echo decorrelation image, subtracting the motion-induced decorrelation value from unity to define a normalization value, and dividing the difference value by the normalization value to define the corrected echo decorrelation value of the corrected echo decorrelation image voxel of the corrected echo decorrelation image volume.

In another aspect of the method, calculating the motion-induced decorrelation value produced by the movement in the reference region of interest may include measuring a maximum decorrelation of a selected area in the reference region of interest.

In another aspect of the method, compensating for the artifactual decorrelation in the echo decorrelation image volume may include defining a second pulse-echo image volume pair that includes a third pulse-echo image volume and a fourth pulse-echo image volume, generating a compensation echo decorrelation image volume from the second pulse-echo image volume pair, and defining a corrected echo decorrelation image volume including a plurality of corrected echo decorrelation image voxels by, for each echo decorrelation image voxel of the echo decorrelation image volume, subtracting an echo decorrelation value of a respective compensation echo decorrelation image voxel of the compensation echo decorrelation image volume from the echo decorrelation value of the echo decorrelation image voxel of the echo decorrelation image volume to define a difference value, subtracting the echo decorrelation value of the respective compensation echo decorrelation image voxel of the compensation echo decorrelation image volume from unity to define a normalization value, and dividing the difference value by the normalization value to generate a corrected echo decorrelation value of a respective corrected echo decorrelation image voxel. In this aspect of the method, adjusting the amount of power provided to the ablation probe based on the echo decorrelation image volume may include adjusting the amount of power based on the corrected echo decorrelation image volume.

In another aspect of the method, the first pulse-echo image volume and the second pulse echo image volume may be captured during ablation, and the third pulse-echo image volume and the fourth pulse echo image volume may be captured before ablation.

In another embodiment of the invention, a system for controlling the ablation process is provided. The system includes one or more processors and a memory coupled to the one or more processors that includes program code. When executed by the one or more processors, the program code causes the system to receive the first plurality of pulse-echo image volumes each including the region of interest, define the first pulse-echo image volume pair that includes the first pulse-echo image volume of the plurality of pulse-echo image volumes and the second pulse-echo image volume of the plurality of pulse-echo image volumes, and generate the echo decorrelation image volume from the first pulse-echo image volume pair. The program code further causes the system to one or more of adjust the amount of power provided to an ablation probe located in the region of interest based on the echo decorrelation image volume, adjust the amount of time power is provided to the ablation probe located in the region of interest based on the echo decorrelation image volume, and/or display the echo decorrelation image volume from the first pulse-echo image volume pair.

In an aspect of the system, the program code may cause the system to adjust the amount of power provided to the ablation probe based on the echo decorrelation image volume by causing the system to derive the control parameter from the echo decorrelation image volume, and adjust the amount of power provided to the ablation probe based on the control parameter.

In another aspect of the system, the program code may cause the system to adjust the amount of power provided to the ablation probe based on the control parameter by causing the system to compare the control parameter to the predetermined threshold, and reduce the amount of power provided to the ablation probe in response to the control parameter exceeding the predetermined threshold.

In another aspect of the system, each pulse-echo image volume may include the plurality of pulse-echo image voxels each having a position within the pulse-echo image volume, the echo decorrelation image volume may include the plurality of echo decorrelation image voxels each associated with a respective pulse-echo image voxel of the plurality of pulse-echo image voxels, and the control parameter may be one of the spatial mean of each echo decorrelation image voxel within the region of interest or the minimum echo decorrelation value of the echo decorrelation image voxels within the region of interest.

In another aspect of the system, the program code may cause the system to derive the control parameter from the echo decorrelation image volume by compensating for the artifactual decorrelation component of the echo decorrelation image volume to generate the corrected echo decorrelation image volume, and deriving the control parameter from the corrected echo decorrelation image volume.

In another aspect of the system, each pulse-echo image volume may include the plurality of pulse-echo image voxels each having a position within the pulse-echo image volume, the echo decorrelation image volume may include the plurality of echo decorrelation image voxels each associated with the respective pulse-echo image voxel of the plurality of pulse-echo image voxels, and the program code may cause the system to generate the corrected echo decorrelation image volume by causing the system to calculate the motion-induced decorrelation value produced by the movement in the reference region of interest, and for each echo decorrelation image voxel of the echo decorrelation image volume, subtract the motion-induced decorrelation value from the echo decorrelation value of the echo decorrelation image voxel to define the difference value, and use the difference value to define the corrected echo decorrelation value of the corrected echo decorrelation image voxel of the corrected echo decorrelation image volume.

In another aspect of the system, the program code may further cause the system to, for each echo decorrelation image voxel of the echo decorrelation image volume, subtract the motion-induced decorrelation value from unity to define the normalization value, and divide the difference value by the normalization value to define the corrected echo decorrelation value of the corrected echo decorrelation image voxel of the corrected echo decorrelation image volume.

In another aspect of the system, the program code may cause the system to calculate the motion-induced decorrelation value produced by the movement in the reference region of interest by causing the system to measure the maximum decorrelation of the selected area in the reference region of interest.

In another aspect of the system, the program code may cause the system to compensate for the artifactual decorrelation in the echo decorrelation image volume by causing the system to define the second pulse-echo image volume pair that includes the third pulse-echo image volume and the fourth pulse-echo image volume, generate the compensation echo decorrelation image volume from the second pulse-echo image volume pair, and define the corrected echo decorrelation image volume including the plurality of corrected echo decorrelation image voxels by, for each echo decorrelation image voxel of the echo decorrelation image volume, subtracting the echo decorrelation value of the respective compensation echo decorrelation image voxel of the compensation echo decorrelation image volume from the echo decorrelation value of the echo decorrelation image voxel of the echo decorrelation image volume to define the difference value, subtracting the echo decorrelation value of the respective compensation echo decorrelation image voxel of the compensation echo decorrelation image volume from unity to define the normalization value, and dividing the difference value by the normalization value to generate the corrected echo decorrelation value of the respective corrected echo decorrelation image voxel. The program code may then cause the system to adjust the amount of power provided to the ablation probe based on the echo decorrelation image volume by adjusting the amount of power based on the corrected echo decorrelation image volume.

In another aspect of the system, the first pulse-echo image volume and the second pulse echo image volume may be captured during ablation, and the third pulse-echo image volume and the fourth pulse echo image volume may be captured before ablation.

In another embodiment of the invention, a computer program product is provided. The computer program product includes a non-transitory computer-readable storage medium, and program code stored on the non-transitory computer-readable storage medium. The program code is configured so that, when executed by one or more processors, the program code causes the one or more processors to receive the first plurality of pulse-echo image volumes each including the region of interest, define the first pulse-echo image volume pair that includes the first pulse-echo image volume of the plurality of pulse-echo image volumes and the second pulse-echo image volume of the plurality of pulse-echo image volumes, and generate the echo decorrelation image volume from the first pulse-echo image volume pair. The program code further causes the one or more processors to one or more of adjust the amount of power provided to an ablation probe located in the region of interest based on the echo decorrelation image volume, adjust the amount of time power is provided to the ablation probe located in the region of interest based on the echo decorrelation image volume, and/or display the echo decorrelation image volume from the first pulse-echo image volume pair.

The above summary presents a simplified overview of some embodiments of the invention to provide a basic understanding of certain aspects of the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

Figure 1:
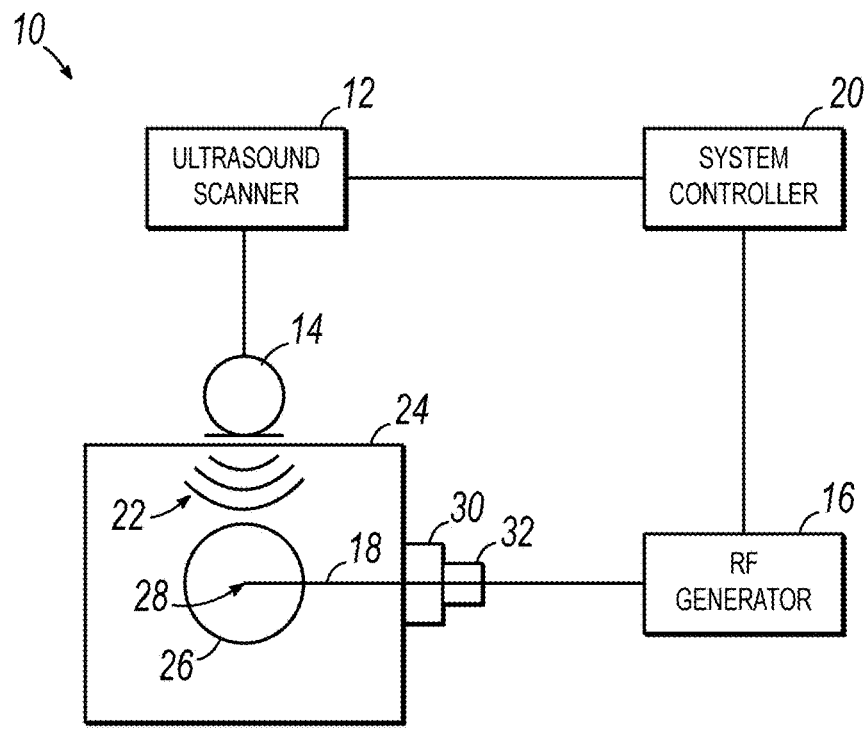
FIG. 1 is a schematic view of an ablation system.

It should be understood that the appended drawings are not necessarily to scale, and may present a somewhat simplified representation of various features illustrative of the basic principles of the invention. The specific design features of the sequence of operations disclosed herein, including, for example, specific dimensions, orientations, positions, and shapes of various illustrated components, may be determined in part by the particular intended application and use environment. Certain features of the illustrated embodiments may have been enlarged or distorted relative to others to facilitate visualization and a clear understanding. In particular, thin features may be thickened, for example, for clarity or illustration.

DETAILED DESCRIPTION

Echo decorrelation imaging is a computationally efficient method of ultrasound imaging that spatially maps heat-induced changes in ultrasound echoes over millisecond time scales. Echo decorrelation imaging may therefore be used to provide feedback on the progress of an ablation while ablation energy is being delivered. To this end, echo changes may be quantified by the local decorrelation of beamformed pulse-echo scan lines, then tracked over the duration of thermal ablation to generate echo decorrelation image volumes, e.g., cumulative echo decorrelation image volumes. These echo decorrelation image volumes may be used as three-dimensional echo decorrelation maps that provide an indication of ablation progress within tissue as it is treated.

Echo decorrelation imaging using three-dimensional ultrasound data is disclosed herein to monitor ablation (e.g., radiofrequency ablation, microwave ablation, bulk ultrasound ablation, high-intensity focused ultrasound, or any other suitable form of ablation) of ex vivo and in vivo tissue. Although ablation is described herein primarily as being radiofrequency ablation for purposes of clarity and brevity, it should be understood that the methods of monitoring and controlling ablation disclosed herein are equally applicable to microwave ablation, bulk ultrasound ablation, high-intensity focused ultrasound ablation, or any other suitable form of treatment that involves heating tissue. Accordingly, embodiments are not limited to radiofrequency ablation.

As used herein, the term "voxel" represents a single data point in a three-dimensional image volume. This data point may consist of a single piece of data, such as a brightness, or multiple pieces of data, such as a color and brightness. Voxels may be defined by a data structure that specifies a value of the voxel (which may be a scalar value or a complex value), and the coordinates of the voxel in the image volume. A voxel generally represents a single point in the image volume, and the space between the voxels is typically not represented by the voxel-based dataset defining the image volume. Depending on the type of data and the intended use for the image volume, this missing information may be reconstructed and/or approximated, e.g., via interpolation, as needed. For example, when performing mathematical operations involving more than one image volume, interpolation or other suitable mathematical methods may be used to adjust the coordinates of one or more of the voxels in one or more of the image volumes to align each voxel in one image volume with a respective voxel in the other image volume. A voxel may include multiple scalar values that define a position, a vector, or any other suitable parameter of the voxel. For example, in ultrasound scans with B-mode and Doppler data, density and volumetric flow rate may be represented as separate channels of data relating to the same voxel positions. An image volume may be defined in a computer system by a data structure including a plurality of voxels that comprise the image volume.

FIG. 1 depicts an ablation system 10 including an ultrasound scanner 12 operatively coupled to an imaging probe 14, a radiofrequency generator 16 operatively coupled to an ablation probe 18, and a system controller 20 configured to operate to the ultrasound scanner 12 and radiofrequency generator 16. The system controller 20 may be configured to operate the ultrasound scanner 12 and radiofrequency generator 16 automatically, in response to input provided by a system operator, e.g., a surgeon or other medical professional, or through a combination of automatic processes and manual inputs. The system controller 20 may also provide information to the system operator regarding an ablation procedure, such as ultrasonic images, tissue or probe temperatures, radiofrequency power settings, etc.

The imaging probe 14 may include a matrix array that utilizes a two-dimensional grid of imaging elements cut from a single piezoelectric crystal. Each imaging element may be configured to transmit and receive pulsed ultrasound signals. A phased pulse may be applied to each individually addressable grid element, and the received echoes may be beam-formed into a composite image. Use of a matrix array can thereby facilitate imaging a full ablation zone at volume rates high enough for real-time imaging.

In operation, the ultrasound scanner 12 may cause the imaging probe 14 to emit ultrasound signals 22 into a tissue sample 24 (e.g., a portion of a patient), and receive reflected ultrasound signals (not shown) from the tissue sample 24.

The matrix array of imaging probe 14 may enable the ultrasound scanner 12 to steer the ultrasound signals 22 along both an azimuthal imaging plane and an elevational imaging plane orthogonal to the azimuthal imaging plane, thereby enabling the acquisition of true real-time three-dimensional pulse-echo image volumes. The reflected ultrasound signals, or "pulse-echo signals" may be processed by the ultrasound scanner 12 to provide an image of a region of interest 26 within the tissue sample 24. This imaging may occur while the ablation probe 18 is inserted into the tissue sample 24 and manipulated such that a tip 28 of ablation probe 18 is positioned within the region of interest 26. To facilitate accurate placement of the tip 28, the ablation system 10 may include a probe guide 30 and/or locking mechanism 32 that guides and locks the ablation probe 18 in position relative to the tissue sample 24. The system operator may use one or more ultrasound images (e.g., real time video) that include the region of interest 26 produced by the ultrasound scanner 12 to guide the position of the tip 28 as it is inserted into the tissue sample 24. Once the tip 28 of ablation probe 18 is properly placed, the radiofrequency generator 16 may be activated, thereby providing an amount of power to the ablation probe 18 sufficient to heat and cause thermal lesioning of at least a portion of the region of interest 26.

Echo decorrelation imaging is a pulse-echo ultrasound imaging technique that spatially maps millisecond-timescale echo-signal decorrelation due to thermal lesioning. The method provides a computationally efficient method of measuring local spectral decoherence in the scattering medium and, accordingly, changes in tissue arising from thermal lesioning. To monitor the thermal ablation process in three dimensions, the echo decorrelation imaging is extended to three dimensions. Computations of echo decorrelation and integrated backscatter maps may thereby be performed within the region of interest 26. The region of interest typically corresponds to a targeted ablation zone, and thus typically includes a spherical region centered on the position of the tip 28 of ablation probe 18.

Figure 2:
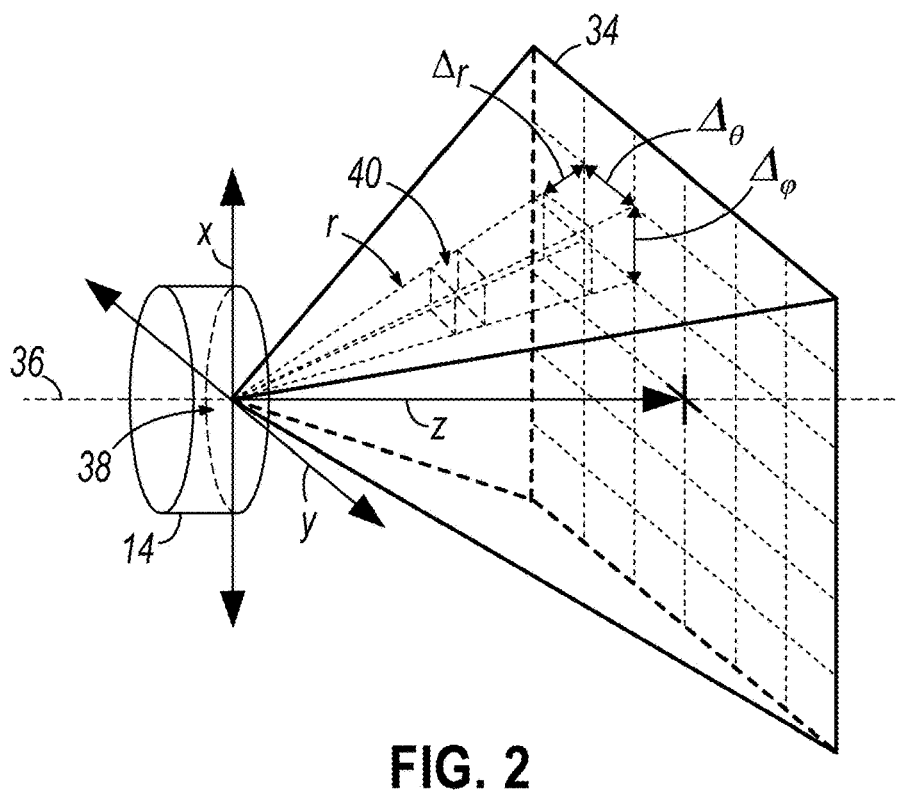
FIG. 2 is a diagrammatic view of a pulse-echo image volume that may be captured by the ablation system of FIG. 1.

FIG. 2 depicts an exemplary image volume 34 (e.g., a pulse-echo image volume) having a pyramidal (frustrum-like) shape with one vertex located on an array axis 36 of imaging probe 14. The array axis 36 of imaging probe 14 may define a z-axis of a coordinate system 38 including a set of unit-length direction vectors. In addition to the z-axis, the unit-length direction vectors of coordinate system 38 may include an x-axis orthogonal to the z-axis, and a y-axis orthogonal to the both the x and z-axes. The x and y-axes may thereby define a plane which is normal to the z-axis and array axis 36. Thus, the x, y, and z-axes of coordinate system 38 form a right-handed coordinate system with an origin located on or proximate to the surface of imaging probe 14.

The pulse-echo image volume 34 may be digitized and stored as a three-dimensional matrix of complex fixed-point numbers each associated with a spatial position defined by pyramidal (frustum-like) coordinate system. Scan lines r may be evenly divided along their lengths, and spaced in equal increments of $\sin(\theta)$ and $\sin(\varphi)$ in the azimuth and elevation directions, respectively. The pulse-echo image volume 34 may thereby be divided into a plurality of voxels 40 (e.g., pulse-echo image voxels) each associated with a quantum of the pulse-echo image volume 34 having a radial dimension $\Delta_r$, an azimuthal dimension $\Delta_\theta$, and an elevation dimension $\Delta_\varphi$. Each pulse-echo image voxel 40 may also have a value that defines a parameter of the pulse-echo image volume 34, e.g., a pulse-echo reflection at the position of the voxel 40 in the pulse-echo image volume 34. Each voxel 40 of the pulse-echo image volume 34 may be represented by a datapoint indexed in the matrix by the radial position of the voxel 40 along scan line r, an azimuthal angle $\theta$ between the scan line r and the x-z plane, and an elevation angle $\varphi$ between the scan line r and y-z plane. Corresponding relations between the above-described pyramidal coordinates (r, $\theta$, $\varphi$) and Cartesian coordinates (x, y, z) are provided by:

$$r = \sqrt{x^2 + y^2 + z^2} \qquad \text{Eqn. 1}$$

$$\sin(\theta) = \left[\frac{y}{\sqrt{y^2 + z^2}}\right] \qquad \text{Eqn. 2}$$

$$\sin(\varphi) = \left[\frac{x}{\sqrt{x^2 + z^2}}\right] \qquad \text{Eqn. 3}$$

Conversions between coordinate systems (or any other calculations disclosed herein) may be performed using floating point numbers to reduce rounding errors. The floating point numbers may be generated from fixed point numbers received from the ultrasound scanner 12.

I(r,t) represents a complex beamformed pulse-echo image volume 34 (e.g., a radiofrequency (Hilbert transformed) pulse-echo signal or baseband demodulated in-phase/quadrature pulse-echo signal) recorded at time t, where r is a coordinate vector in Cartesian space. I(r, t+τ) may then represent a second pulse-echo image volume 34 recorded at time t+τ, where τ is the inter-frame time. A spatially windowed zero-lag cross-correlation between the two pulse-echo image volumes 34 may be computed as:

$$R_{01}(r) = \langle I(r,t) \cdot I(r,t+\tau)^* \rangle \qquad \text{Eqn. 4}$$

where * denotes complex conjugation and < > denotes a windowed spatial integration. Spatial integration over a finite window maybe equivalent to convolution of the pulse-echo image volume 34 with the windowing function, defined as follows:

$$\langle I(r,t) \rangle = \int_S w(r-r') I(r,t) = I(r,t) * w \qquad \text{Eqn. 5}$$

where w is the windowing function and S is the coordinate space of the pulse-echo image volume 34 over which the quantity is integrated. This may allow for efficient computation of echo decorrelation image volumes using a finite impulse response (FIR) filter or fast Fourier transform (FFT) based convolution, which may be preferred for use in real-time imaging. The term "echo decorrelation image volume" refers to an image volume that defines changes to the echo signal between a pair of time-spaced pulse-echo image volumes 34.

The windowed zero-lag autocorrelation of each pulse-echo image volume 34 may be computed in a similar fashion, $$R_{00}(r) = \langle |I_0(r,t)|^2 \rangle \qquad \text{Eqn. 6}$$

$$R_{11}(r) = \langle |I_0(r,t+\tau)|^2 \rangle \qquad \text{Eqn. 7}$$

and can be regarded as a smoothed map of local backscatter energy magnitudes for each pulse-echo image volume 34. The elementwise geometric mean of the autocorrelation functions may then be defined as an integrated backscatter map, $\beta(r)$ $$\beta(r) = \sqrt{R_{11} \cdot R_{00}} \qquad \text{Eqn. 8}$$

which approximates local tissue backscatter energy between the two pulse-echo image volumes 34.

A simplified locally normalized echo decorrelation image volume may be defined as the normalized correlation coefficient between the pulse-echo image volumes subtracted from unity as follows:

$$\Delta(r)_{local} = 1 - \frac{|R_{01}(r)|^2}{|R_{11}(r)| \cdot |R_{00}(r)|} = 1 - \frac{|R_{01}(r)|^2}{\beta^2(r)} \qquad \text{Eqn. 9}$$

This expression may be used as an approximation of local spectral decoherence in the scattering medium. Accordingly, echo decorrelation imaging may provide a computationally inexpensive method of measuring changes in the scattering medium induced by thermal lesioning. Normalization may be performed by spatially averaging the backscattered energies $\beta(r)$ to account for artifactual decorrelation in regions of both high and low echogenicity. The quantity may then be divided by the inter-frame time $\tau$ to account for greater variation within a larger time window. An exemplary echo decorrelation image volume is provided by, $$\Delta(r) = 2\left[\frac{\beta^2(r) - |R_{01}(r)|^2}{\tau \cdot \left[\beta^2(r) + \overline{\beta^2}\right]}\right] \qquad \text{Eqn. 10}$$

where the term $\overline{\beta^2}$ is the spatial mean of the integrated backscatter map over the entire pulse-echo image volume 34. This may be used in place of normalization by $\overline{\beta^2}$ to account for the backscatter energies of both pulse-echo image volumes 34 of a pulse-echo image volume pair.

The numerator $(\beta^2(x,y,z,t) - |R_{01}(x,y,z,t)|^2)$ may provide an indication of transient heat-induced changes in each voxel 40 of the pulse-echo image volume 34. Accordingly, in regions where the signal has diverged between volumes, decorrelation may be larger, and in regions where the signal is similar between volumes, decorrelation may be smaller. To account for stochastic variation within a given adjacent pair of pulse-echo image volumes 34, instantaneous echo decorrelation image volumes can be computed from an ensemble average of multiple pulse-echo image volume pairs. Ensemble averaged instantaneous echo decorrelation $\overline{\Delta}(r,t)$ may be computed as:

$$\overline{\Delta}(r,t) = \frac{1}{K-1}\sum_{k=1}^{K-1}\Delta(r,k\tau) \qquad \text{Eqn. 11}$$

where K is the number of pulse-echo image volumes over which the ensemble average is computed and k is the index of each pulse-echo image volume.

Numerical analysis of the effect of ensemble averaging shows that root-mean-square (RMS) error between echo decorrelation imaging and scatterer reflectivity decoherence is proportional to $1/\sqrt{N}$ for small windows, where N is the number of ensemble-averaged pulse-echo image volumes 34. Accordingly, ensemble averaging may significantly reduce the effect of random variation on echo decorrelation image volumes. Using a larger spatial window may also improve resilience to stochastic variation. For three-dimensional echo decorrelation, where the large amount of data may limit ensemble averaging, a larger window can be used to account for stochastic variation. However, the use of larger windows may reduce spatial resolution, as windowing can introduce statistical dependence to the computed echo decorrelation image volumes.

Monitoring of thermal ablation procedures may be accomplished by computing a cumulative echo decorrelation image volume $\Delta_{cum}(r)$ from a series of instantaneous echo decorrelation image volumes. B-mode images may be captured at a set interval and their instantaneous echo decorrelation computed from Equation 10 and ensemble averaged as defined by Equation 11. The cumulative echo decorrelation image volume $\Delta_{cum}(r)$ may then be computed as an element-wise maximum of all instantaneous echo decorrelation image volumes, $$\Delta_{cum}(r) = \max(\Delta(r,0),\Delta(r,1),\ldots \Delta(r,N)) \qquad \text{Eqn. 12}$$

where N is the number of instantaneous echo decorrelation image volumes computed thus far. The cumulative maximum echo decorrelation image volume may measure the total heat-induced echo signal decorrelation at a given voxel 40, giving an estimate of local tissue necrosis due to thermal treatment. Advantageously, echo decorrelation mapping may offer better predictive power for measurement of thermal lesioning than backscatter mapping.

In some cases, it may be advantageous to isolate thermal decorrelation caused by thermal effects from artifactual decorrelation arising from other sources, such as motion and noise. The total or "uncorrected" decorrelation of each voxel may be modeled as a linear combination of thermal decorrelation and artifactual decorrelation as follows, $$\Delta(r,t) \approx 1 - \rho(r,t)(1 - \Delta(r,t)_{artifactual}) \qquad \text{Eqn. 13}$$

where $\rho$ represents a multiplicative scale factor associated with artifactual decorrelation sources as a function of time t and position r.

The parameter $\rho$ may be estimated by recording a set of pulse-echo image volumes 34 prior to ablation, and generating a compensation echo decorrelation image volume $\Delta_{comp}$ from a cumulative echo decorrelation image volume generated from the pre-ablation pulse-echo image volumes 34. The derived quantity may be determined as:

$$\Delta_{corr}(r,t) = \frac{\Delta(r,t) - \Delta_{comp}(r,t)}{1 - \Delta_{comp}(r,t)} \qquad \text{Eqn. 14}$$

In Equation 14, $\Delta(r,t)$ may represent an uncorrected echo decorrelation image voxel at position r in the uncorrected echo decorrelation image volume $\Delta(t)$. The echo decorrelation value of this voxel $\Delta(r,t)$ may include an unwanted artifactual component, e.g., a motion component. Likewise, $\Delta_{comp}(r,t)$ may represent a compensation echo decorrelation image voxel at position r in the compensation echo decorrelation image volume $\Delta_{comp}(t)$ generated from pulse-echo image volumes 34 recorded prior to ablation. Subtracting the compensation echo decorrelation image voxel $\Delta_{comp}(r,t)$ from a respective uncorrected echo decorrelation image voxel $\Delta(r,t)$ having the same position r may produce a difference value associated with position r. Subtracting the echo decorrelation value of compensation echo decorrelation image voxel $\Delta_{comp}(r,t)$ from unity may produce a normalization value associated with position r, which may be used to normalize the difference value. Voxel $\Delta_{corr}(r,t)$ may represent a corrected echo decorrelation image voxel at position r in the corrected echo decorrelation image volume $\Delta_{corr}(t)$. The corrected echo decorrelation image volume $\Delta_{corr}(t)$ may represent the echo decorrelation attributed primarily to changes in the scattering medium (e.g., the thermal component of the echo decorrelation) at time t.

Accordingly, each voxel $\Delta_{corr}(r,t)$ of corrected echo decorrelation image volume $\Delta_{corr}(t)$ may have a corrected echo decorrelation value associated with position r in the corrected echo decorrelation image volume $\Delta_{corr}(t)$. Alternatively, corrected echo decorrelation $\Delta_{corr}(r,t)$ may be computed as the difference $\Delta(r,t) - \Delta_{comp}(r,t)$.

A real-time closed-loop feedback control process that uses a control parameter (e.g., a scalar control parameter) derived from cumulative echo decorrelation image volumes may be used to control the power and/or duration of an ablation process. The control parameter may be updated each time the cumulative echo decorrelation is updated and compared to a predetermined threshold. In response to the control parameter exceeding the predetermined threshold, the control process may reduce the power output $P_{out}$ of radiofrequency generator 16, e.g., by setting $P_{out}=0$.

By way of example, a control parameter $\hat{\Delta}$ may be derived from a cumulative maximum echo decorrelation image volume $\Delta_{cum}(r)$ as a spatial mean of all datapoints (e.g., voxel decorrelation values) within a selected region of interest 26, as shown below:

$$\hat{\Delta}_{avg} = \frac{1}{|\mathcal{R}|} \sum_{r \in \mathcal{R}} \Delta_{cum}(r, n) \qquad \text{Eqn. 15}$$

In an alternative embodiment, the control parameter $\hat{\Delta}$ may be derived from the cumulative maximum echo decorrelation image volume as the minimum echo decorrelation value within the region of interest 26, as shown below:

$$\hat{\Delta}_{min} = \min(\hat{\Delta}(r,n)), r \in \mathcal{R} \qquad \text{Eqn. 16}$$

The control parameter $\hat{\Delta}$ may also be derived as the maximum $\hat{\Delta}_{max} = \max(\hat{\Delta}(r,n)), r \in \mathcal{R}$ or as another mathematical function of the echo decorrelation within the region of interest 26. In each case, $\mathcal{R}$ may denote the set of voxels 40 within the targeted region of interest 26, and $|\mathcal{R}|$ may be the number of voxels 40 within the region of interest 26. As described above, ablation may be stopped in response to the control parameter $\hat{\Delta}$ exceeding a threshold, or ablation may be extended in response to the control parameter $\hat{\Delta}$ failing to exceed a threshold.

In an alternative embodiment, the control parameter $\hat{\Delta}$ may be used as an input to a proportional-integral-derivative (PID) type controller that controls the power output of the radiofrequency generator 16. In this embodiment, the control parameter $\hat{\Delta}$ may be subtracted from a threshold value to generate a proportional error signal. The proportional error signal may be integrated to generate an integral error signal, and differentiated to generate a derivative error signal. Each of the proportional, integral, and derivative signals may then be weighted according to a control algorithm, and the weighted signals summed to produce a control signal for controlling the power output of the radiofrequency generator 16.

In operation, pulse-echo image volume pairs may be acquired as complex in-phase/quadrature pulse-echo image volumes 34 using a matrix array imaging probe 14. Received pulse-echo image volumes 34 may then be used to create a three-dimensional cumulative echo decorrelation image volume. The control parameter $\hat{\Delta}$ may be derived from the cumulative echo decorrelation image volume and used to control the duration and/or power levels of ablation using the system controller 20. The system controller 20 may include both hardware and software configured to coordinate acquisition of the pulse-echo image volumes 34 from the ultrasound scanner 12, generate the echo decorrelation image volume, and automatically control of the radiofrequency generator 16.

Figure 3:
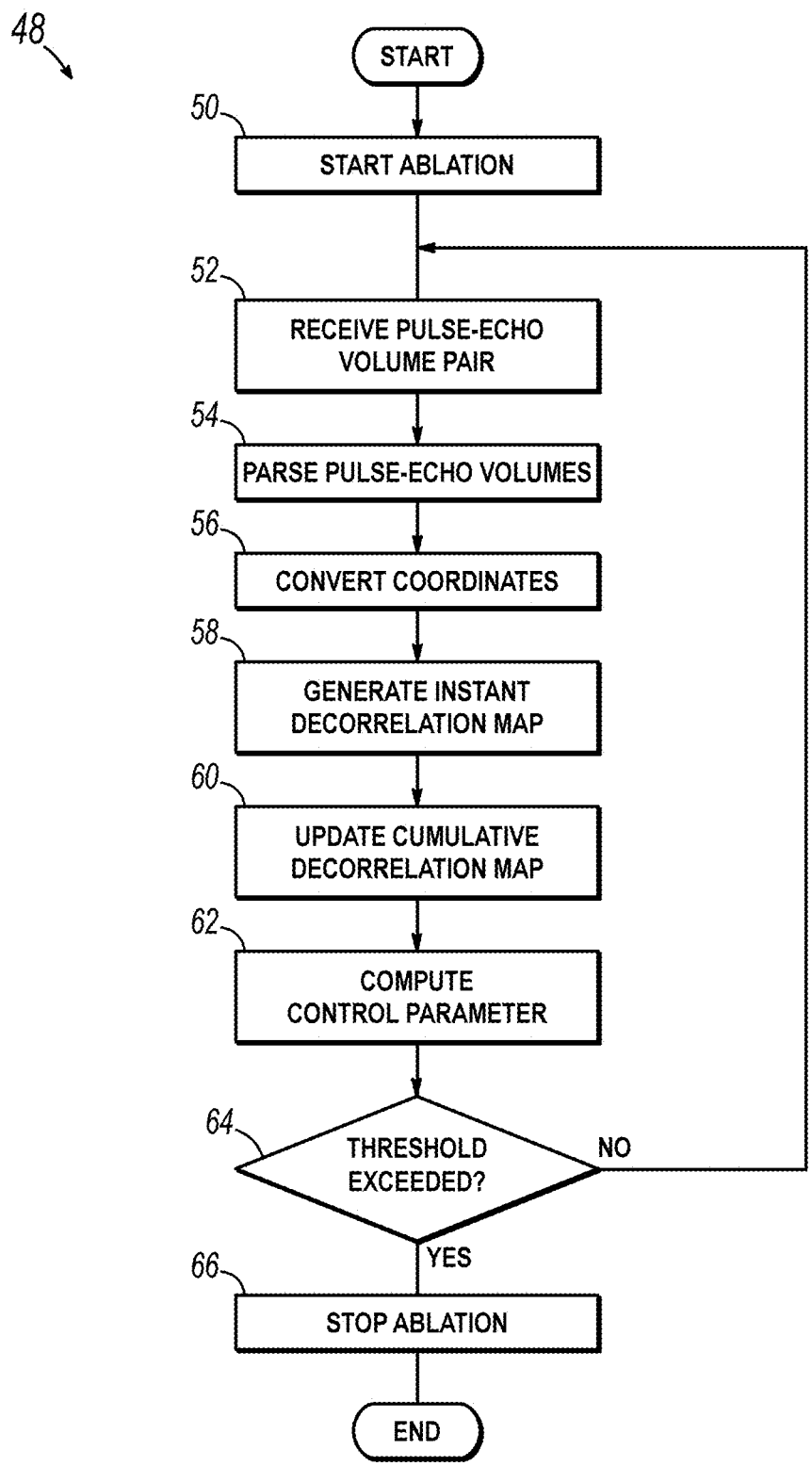
FIG. 3 is a flowchart of a process for controlling an ablation that may be performed by the ablation system of FIG. 1.

FIG. 3 depicts a flowchart illustrating an ablation monitoring process 48 that may be implemented by one or more of the ultrasound scanner 12, system controller 20, or another suitable computing device. In block 50, the process 48 starts an ablation, e.g., by causing the ultrasound scanner 12 to begin capturing pulse-echo image volumes 34 from a patient or tissue sample. These pulse-echo image volumes 34 may include pre-ablation volumes for use as a baseline. The process 48 may also cause the radiofrequency generator to begin providing a radiofrequency signal (e.g., 150 watt signal) to the ablation probe 18. In block 52, the process 48 receives a pulse-echo image volume pair, e.g., from the ultrasound scanner 12. In response to receiving the pulse-echo image volume pair, the process may proceed to block 54, and parse each pulse-echo image volume 34 of the pair into readable volume data. In block 56, the process 50 may convert the volume data from one coordinate system into another (e.g., from pyramidal coordinates ($r$, $\theta$, $\varphi$) into Cartesian coordinates ($x$, $y$, $z$)). The process 50 may then proceed to block 58 and generate an instant echo decorrelation image volume (i.e., instantaneous decorrelation map) from the current pulse-echo image volume pair. In block 60, the process 50 may use the instantaneous echo decorrelation image volume to update the cumulative echo decorrelation image volume (i.e., cumulative decorrelation map). The process 50 may then proceed to block 62 and generate the control parameter $\hat{\Delta}$, e.g., the average decorrelation within the region of interest 26.

In block 64, the process 50 determines if the control parameter has exceeded a predetermined threshold. If the control parameter has not exceeded the predetermined threshold ("NO" branch of decision block 64), the process 50 may return to block 52 and continue receiving pulse-echo image volume pairs. If the control parameter has exceeded the predetermined threshold ("YES" branch of decision block 64), the process 50 may proceed to block 66 and stop the ablation, e.g., by shutting of the radiofrequency generator 16 and/or stopping the further generation of pulse-echo image volumes 34.

By way of example, ultrasound pulse-echo image volumes 34 may be recorded using a suitable ultrasound scanner 12 (e.g., a Siemens SC2000) and imaging probe 14 (e.g., 4Z1c matrix array probe having a transducer matrix including 48×36 elements that provides an active aperture 19.2×14.4 mm$^2$, and having bandwidth 1.5-3.5 MHz). Each pulse-echo image volume 34 may comprise an in-phase/quadrature phase demodulated three-dimensional matrix of complex fixed-point numbers in a pyramidal (frustum-like) coordinate system. The voxels 40 may be defined by datapoints indexed by the position of the voxel along each scan line r, the azimuthal angle $\theta$, and the elevational angle $\varphi$. Scan lines may be spaced in equal increments of $\sin(\theta)$ and $\sin(\varphi)$. The radiofrequency generator 16 may generate a signal having a center frequency $f_c$ (e.g., $f_c$=2.8 MHz) and a sampling rate $f_s$ (e.g., $f_s$=2.5 MHz) for in-phase/quadrature (i.e., complex) demodulated echo-pulse signals. As noted above, conversions between coordinate systems may be performed using floating point numbers generated from fixed point numbers to reduce rounding errors.

Imaging depth and scan angles may be selected based on the size of the region of interest 26 and the specifications of the ultrasound scanner 12 and imaging probe 14. A typical scan volume may have elevational and azimuthal scan angles of about 78 degrees and a nominal depth of 110 mm, with true recorded depths extending to 117 mm. An exemplary size of the pyramidal space volumes for the above specified ultrasound scanning equipment may be 376×55×54×2 (r×θ×φ×2 pulse-echo image volumes), with a frame rate of 55 volumes per second, and a time between acquisitions of approximately 16 seconds. As a practical matter, using higher spatial resolutions to image the ablation zone may reduce the time resolution and vice-versa, although this tradeoff may vary depending on the performance of the equipment used. In each case, a large enough volume having a minimum of four vertexes may be scanned to provide a buffer space isotropically around the region of interest 26 to account for edge effects at the boundaries of the scanned volume. A typical scan setting may be 56×56 azimuth and elevation scan angles, with a nominal depth of 70 mm (actual volumes extended to 80 mm). Received echo-pulse volume matrix sizes for this setting were 255×45×42×2, with a volume rate of 117 volumes per second and a volume export rate of once every 6 seconds.

Exported volumes may be scan converted onto a Cartesian grid having an isotropic step size (e.g., 1 mm) using trilinear interpolation. The Cartesian grid may be sized so that it fully encloses the pulse-echo image volume 34, where the Cartesian dimension z is the distance from the origin in the depth direction, and dimensions y and x are the distances along the elevational and azimuthal directions, respectively, centered at the origin. Each point on the Cartesian grid $\hat{x}_i$ may be sampled and its corresponding position in pyramidal space determined using Equations 1-3.

The position and value of each Cartesian point $x_i$ in pyramidal space $(\hat{r}_i=(r_i,\theta_i,\varphi_i)$ may be determined in the Cartesian space by weighting the m closest points (e.g., m=8 points) in a cubic lattice surrounding the sampled point by their distance and determining the weighted sum, $$I_{cart}(x_i) = \sum_{n=1}^{m} c_n(r_n, \hat{r}_i) \cdot I_{pyram}(r_n) \qquad \text{Eqn. 17}$$

where $I_{pyram}$ is the pulse-echo image volume 34 in pyramidal coordinates, $I_{cart}$ is the pulse-echo image volume 34 frame in Cartesian coordinates, and $c_i$ is the coefficient of each pyramidal space voxel 40 as determined by its distance from the sampled point $\hat{r}_i$.

Echo decorrelation image volumes may be determined as described above. Spatially averaged quantities within a window may be computed via convolution, allowing for efficient discrete computation of decorrelation with FIR filtering or FFT-based methods. Spatial frequency domain convolution may offer better performance for a particular setup, in which case it may be preferable to complete the convolution operations in the frequency domain.

By way of example, each zero-padded correlation term R[x] may be defined in a discrete three-dimensional Cartesian coordinate system as:

$$\langle R[x] \rangle = \sum_{x \in V} R[x] \cdot w[x-x_0] = R[x] \circledast w[x] = \mathcal{F}^{-1}[\mathcal{F}[R[x]]] \circ \mathcal{F}[w[x]] \qquad \text{Eqn. 18}$$

where x is the coordinate vector in discrete cartesian space, $\circledast$ is circular convolution, $\circ$ is the elementwise product, and w is a three-dimensional Gaussian kernel with correlation window width parameter σ (e.g., σ=3 mm), defined with its Fourier transform pair as:

$$w[x] = \frac{1}{\sigma^3 (2\pi)^{3/2}} \cdot \exp\left(-\frac{|x^2|}{2\sigma^2}\right) \overset{FT}{\leftrightarrow} \exp\left(-\frac{\sigma^2|k^2|}{2}\right) \qquad \text{Eqn. 19}$$

where k corresponds to the frequency bin vector in the three-dimensional spatial frequency domain.

A three-dimensional Gaussian kernel with width parameter σ=3 mm may be selected for the windowing function as a compromise between the spatial resolution of the computed echo decorrelation image volumes and the reduction of the effects of stochastic variation. However, it should be understood that embodiments of the invention are not limited to any particular correlation window width parameter σ. In cases where ensemble averaging is used, a smaller correlation window width parameter σ may be selected (e.g., 1≤σ≤2.5 mm) due to a reduced need for smoothing.

Each correlation term $R_{01}$, $R_{00}$, and $R_{11}$ as defined in Equations 4, 6, and 7 may be transformed into the frequency domain using a suitable commercially Fourier domain transformation function. The frequency domain correlation terms may then be pointwise multiplied with a suitable window (e.g., a Gaussian window) defined in the frequency domain. The windowed functions may then be transformed back to the spatial domain, and used in the definition of decorrelation. In an alternative embodiment, convolution functions may be used in the time domain to achieve essentially the same results.

Echo decorrelation artifacts may be caused by tissue motion and electronic noise. For example, cardiac motion may have a peak of about 60 mm/second during the systolic portion of the cardiac cycle, and 0-20 mm/second during the diastolic portion of the cardiac cycle. To correct for motion-induced artifacts in echo decorrelation, motion-induced decorrelation $\Delta_M(r,t)$ may be measured within a reference region of interest (e.g., a x×y mm² area, or a x×y×z mm³ volume where x, y, and z are in the range of 4-6 mm, depending on the size of the ablation zone 92) proximate to the tip 28 of the ablation probe 18 (e.g., 10-15 mm from the tip 28). Motion effects may then be removed from the echo decorrelation image volume by substituting the maximum motion-induced decorrelation value $\Delta_{M\_max}$ into Equation 14 for $\Delta_{comp}(r,n)$ to produce:

$$\Delta_{corr}(r,n) = \frac{\Delta(r,n) - \Delta_{M\_max}}{1 - \Delta_{M\_max}} \qquad \text{Eqn. 20}$$

In alternative embodiments, correction may be performed using the subtraction $\Delta_{corr}(r,n)=\Delta(r,n)-\Delta_{M\_max}$. Further, the maximum decorrelation $\Delta_{M\_max}$ may be replaced by the mean value, maximum value, or another mathematical function of $\Delta_M$ within the reference region of interest. Further compensation for baseline decorrelation may be measured before ablation. The cumulative decorrelation may then be computed for the temporal maximum using Equation 12 as shown:

$$\Delta_{corr,cum}(r,n) = \max_n(\Delta_{corr}(r,n)) \qquad \text{Eqn. 21}$$

EXPERIMENTAL RESULTS—EX VIVO BOVINE LIVER

Three dimensional echo decorrelation imaging was implemented and tested on radiofrequency ablation of ex vivo bovine liver tissue. These tests employed three-dimensional ultrasound imaging using a clinical ultrasound scanner having volumetric frame rates comparable to those of two-dimensional ultrasound. However, compared to two-dimensional echo decorrelation imaging, the three-dimensional configuration required sparser spatial sampling of the pulse-echo image volume 34, as well as acquisition of much larger echo data sets, thus limiting both spatial and temporal resolution. Receiver operating characteristic curve analysis was used to quantify the success of local ablation predictions. Secondary analyses correlated local echo decorrelation with corresponding local tissue temperatures, and tested the prediction of ablation volumes using weighted K-means clustering on three-dimensional echo decorrelation image volumes and integrated backscatter maps. Toward optimization of real-time thermal ablation monitoring, these analyses were performed and compared for three alternative types of echo decorrelation image volumes each employing different normalization approaches, as well as for integrated backscatter based approaches.

Figure 4:
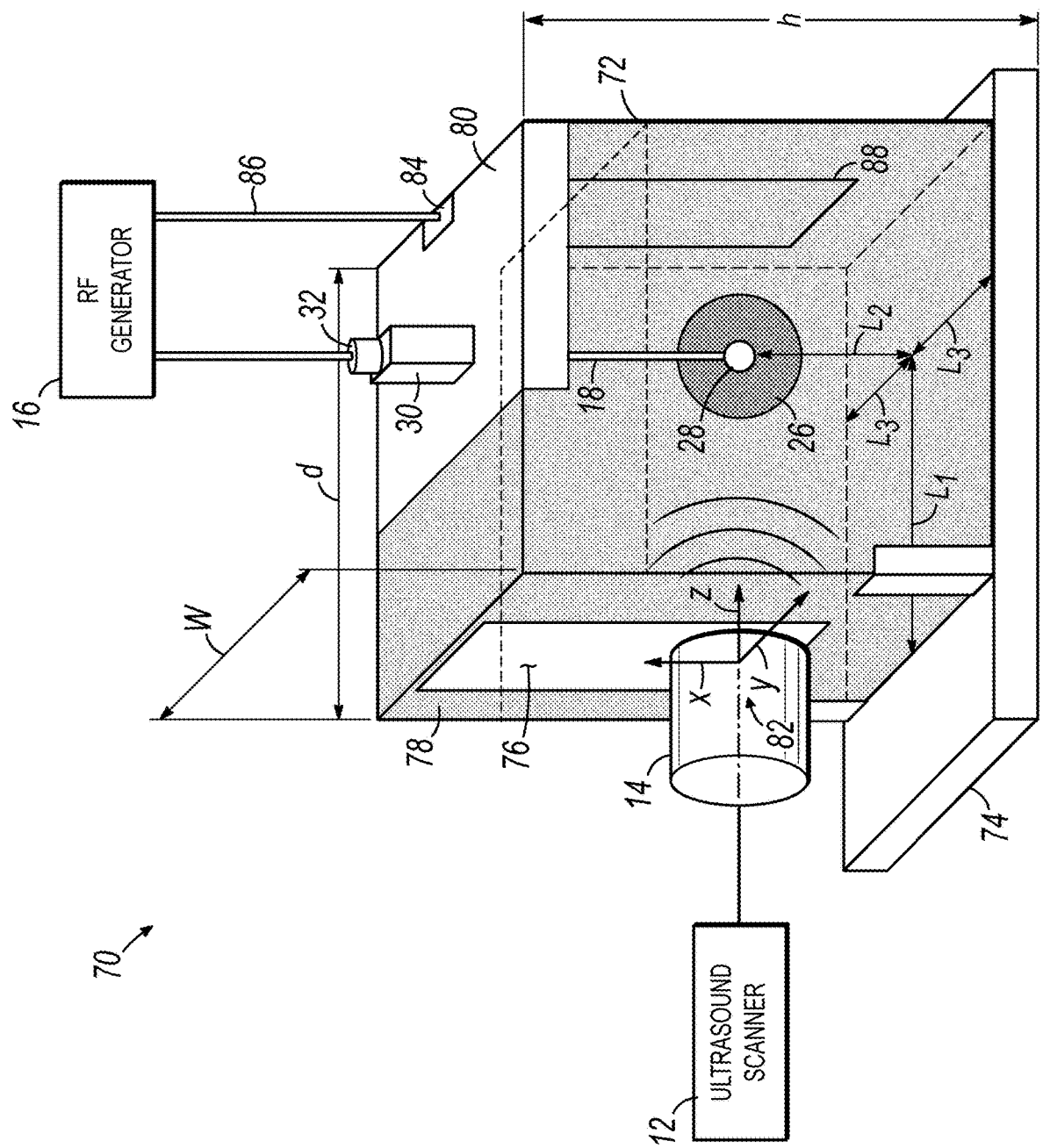
FIG. 4 is a schematic view of a test environment for testing ablation processes, such as the process of FIG. 3, in tissue samples.

FIG. 4 depicts an exemplary test environment 70 for radiofrequency ablation guided by three-dimensional ultrasound imaging. The test environment 70 includes a sample container 72 (e.g, a cuvette having a height h=100 mm, a width w=82 mm, and a depth d=82 mm) and a stand 74 configured to support the sample container 72. The sample container 72 and stand 74 were designed using computer aided design software and 3D-printed with a polylactic acid filament. The sample container 72 includes an acoustic window 76 for placement of an imaging probe 14, and was sealed with a film 78, e.g., Tegaderm film adhesive membrane. Tegaderm film adhesive membranes are available from the 3M Corporation, of St. Paul, Minnesota. During testing, the top of sample container 72 was partially covered by a lid 80 including an integrated probe guide 30 having a length of about 60 mm. The probe guide 30 is configured to receive an ablation probe 18, such as a RITA StarBurst™ XLi-enhanced device with micro-infusion, which is available from AngioDynamics of Latham, NY.

During testing, the ablation probe 18 was inserted straight into the tissue samples 24 under test. A locking mechanism 32 operatively coupled to the ablation probe 18 was configured to control insertion of the ablation probe 18 to a predetermined depth such that the tip 28 of ablation probe 18 was 60 mm from the inner surface of the lid 80. This insertion depth resulted in the tip 28 of ablation probe 18 being located at a distance $L_1$ of approximately 52 mm from the acoustic window 76 (and thus the surface of imaging probe 14), a distance $L_2$ of approximately 40 mm from the bottom surface of the sample container 72 (in the x or elevation direction), and a distance $L_3$ of approximately 42 mm from the sides of the sample container 72 (in the y or azimuth direction). The dimension between the imaging probe 14 and the tip 28 of ablation probe 18 is referred to as the z or range direction, the dimension between the imaging probe 14 and the sides of the sample container 72 is referred to as the y or azimuth direction, and the dimension between the imaging probe 14 and the bottom/top of the sample container 72 is referred to as the x or elevation direction. During testing, the tip 28 of ablation probe 18 was centered on the axis of the ultrasound array of imaging probe 14 with a positioning uncertainty of about 1 mm.

The x, y, and z-directions are shown by a reference frame 82, which is defined by set of unit-length direction vectors coextensive with those of coordinate system 38. The unit-length vectors of the reference frame 82 include an x-axis parallel to the above described x-direction, a y-axis orthogonal to the x-axis and parallel to the above described y-direction, and a z-axis parallel to the above described z-direction and orthogonal to both the x and y-axes. The x, y, and z-axes thereby form a right-handed coordinate system for defining the positions of the tip 28 of ablation probe 18 and regions of interest 26 within the sample container 72. The origin of the reference frame 82 may define a point with coordinates of (0,0,0), and may be located on the surface of the imaging probe 14 along the axis of the ultrasound array so that every point within the sample has a coordinate value relative to the imaging probe 14.

The lid 80 includes an opening 82 behind the probe guide 30 that provides a passage for an electrical ground conductor 86 which operatively couples an electrical ground of the radiofrequency generator 16 to a grounding pad 88. The grounding pad 88 used during testing included clinical dispersive electrodes (e.g., RITAVR Thermopads, available from AngioDynamics, Manchester, Georgia), which are specified for use with the radiofrequency generator 16 and ablation probe 18 of the test environment 70. The stand 74 includes integrated mounts for the imaging probe 14 and the sample container 72, and is configured to keep both secured in the intended geometry while also enabling rapid switching between ablation experiments.

Fresh whole bovine liver was obtained from a local slaughterhouse and kept in ice inside a cooler during transport to the laboratory for ablation experiments. The liver was stored in a sealed bag on the benchtop for less than 30 min to acclimate to room temperature, e.g., a temperature between 20° C. and 25° C. Liver tissue was then cut into roughly cubic tissue samples 24 fitting the width and length of the sample container 72 (e.g., a height of 70-90 mm). The tissue samples 24 were placed into the sample container 72 with the grounding pad 88 bounding the edge of the tissue sample 24 distal from the imaging probe 14. After securing the stand 74 in place using a three-dimensional positioning arm, the sample container 72 containing the bovine liver tissue sample 24 was placed and locked onto the stand 74. To minimize air bubbles within the tissue sample 24, phosphate-buffered saline (0.01 M, having a pH 7.4 at 25° C. and made with P3813 powder available from Sigma Life Science, St. Louis, MO) was poured into the sample container 72 while the tissue sample 24 was manually manipulated. This process allowed saline to penetrate empty blood vessels in the tissue sample 24. The ablation probe 18 was inserted through the probe guide 30 and into the tissue sample 24. Once in position, the ablation probe 18 was secured with another three-dimensional positioning arm (not shown). The tines of ablation probe 18 were then deployed to a 20 mm diameter and the ground conductor 86 connected to the grounding pad through the opening 84 of lid 80.

A plurality of ablation exposures (N=14 exposures) were performed using a RITAVR 1500X RF Generator, available from AngioDynamics of Manchester, GA, as the radiofrequency generator 16. The output of the radiofrequency generator 16 was set to a nominal power of 150 W and a target temperature of 105° C. The duration for maintaining this target temperature, averaged between three thermocouples located within the tips of the ablation probe tines, was set to five minutes in the radiofrequency generator 16. The resulting duration of each ablation procedure was about ten minutes, including approximately two minutes of initial heating, five minutes of the tissue being held at the target temperature, and two minutes of cooldown.

Throughout each procedure, time-dependent temperatures were recorded automatically by the radiofrequency generator 16 based on signals received from four thermocouples integrated into the ablation probe 18. These thermocouples included three thermocouples within the tine tips, as well as a fourth thermo-couple extending from the tip 28 of ablation probe 18. The time dependent temperature data was acquired from an RS232 port output of the radiofrequency generator 16 at a sampling rate of 10 Hz using a custom program run on a laptop computer serving as the system controller 20. Data packets, which also included output of elapsed time, instantaneous electrical power, measured tissue impedance, and generator mode parameters, were acquired by the computer, filling a buffer after detection of a specific character sequence ending with a "^C" (end of text) character within the serial data stream. Temperature values, output as 14-bit integers stored within two-byte words after scaling by a factor of 10, were parsed to record time-dependent temperature measurements from each thermocouple with 0.1° C. precision.

After each ablation procedure, a fitted sliding cover was inserted into the acoustic window 76 of sample container 72 and a tightly fitting lid was placed on the top opening of the sample container 72, both of which constrained expansion of the tissue sample 24 during freezing. The sample container 72 was then placed in a freezer at a temperature of −80° C. for at least twelve hours. After removal from the freezer, the window cover and lid were removed.

Figure 5:
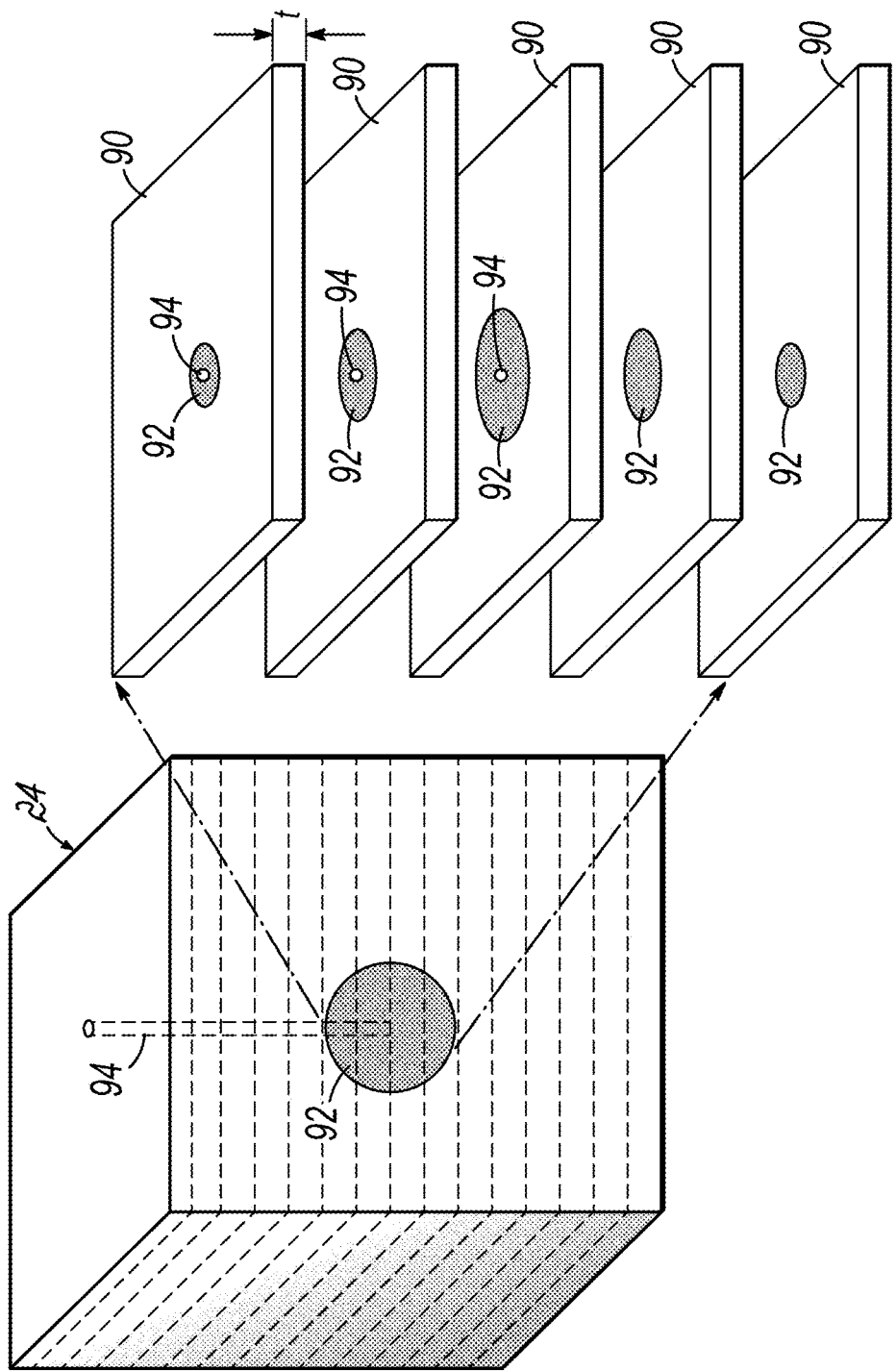
FIG. 5 is a diagrammatic view of an ablated test sample showing a process for evaluating experimental results obtained from the test environment of FIG. 4.

FIG. 5 depicts a sectioning process applied to the frozen tissue samples 24. For use as a height reference, multiple parallel marks were made on the surface of the tissue sample 24 within the window at intervals of five millimeters using a scalpel and ruler. Once the parallel marks were made, the tissue samples 24 were sectioned into parallel tissue sections 90, starting from the bottom of the tissue samples 24 and using a commercial meat slicer. The parallel marks on the vertical tissue block surface were used as distance references for the observable top and bottom of an ablation zone 92, which was assessed based on gross discoloration. The average tissue section thickness t for each experiment was about three millimeters, which was determined from the number of tissue sections 90 covering this measured span. The elevational position of the tip 28 of ablation probe 18 was determined from the bottom-most tissue section 90 in which a probe track 94 could be observed. This elevation position within the tissue sample 24 was registered to the known elevation position of the tip 28 of ablation probe 18, level with the ultrasound array axis of imaging probe 14, and 40 mm from the inner bottom surface of the sample container 72. Since water content within the ablation zone 92 was small compared to the surrounding liver parenchyma, expansion of the ablation zone 92 due to freezing was neglected.

After sectioning, the tissue sections 90 were optically scanned at a resolution of 240 dpi using a V550 scanner, which is available from Epson America, Inc. Long Beach, CA. Scanned tissue sections 90 were then segmented using a custom tissue segmentation graphical user interface. Within this graphical user interface, the scanned image of each tissue section 90 was manually translated and rotated to best match a fixed square outline corresponding to the cross section of the sample container 72. Ablation zones 92 were primarily segmented automatically using an empirically defined brightness threshold to determine the ablated region. In a few trials, manual segmentation was performed due to ambiguities in image brightness caused by large vessels near the boundaries of the ablation zone 92. A three-dimensional map of the ablation zone 92 was then reconstructed using nearest-neighbor interpolation onto a grid with an isotropic step size of one millimeter for direct comparison to three-dimensional echo decorrelation image volumes and integrated backscatter maps.

Figure 6:
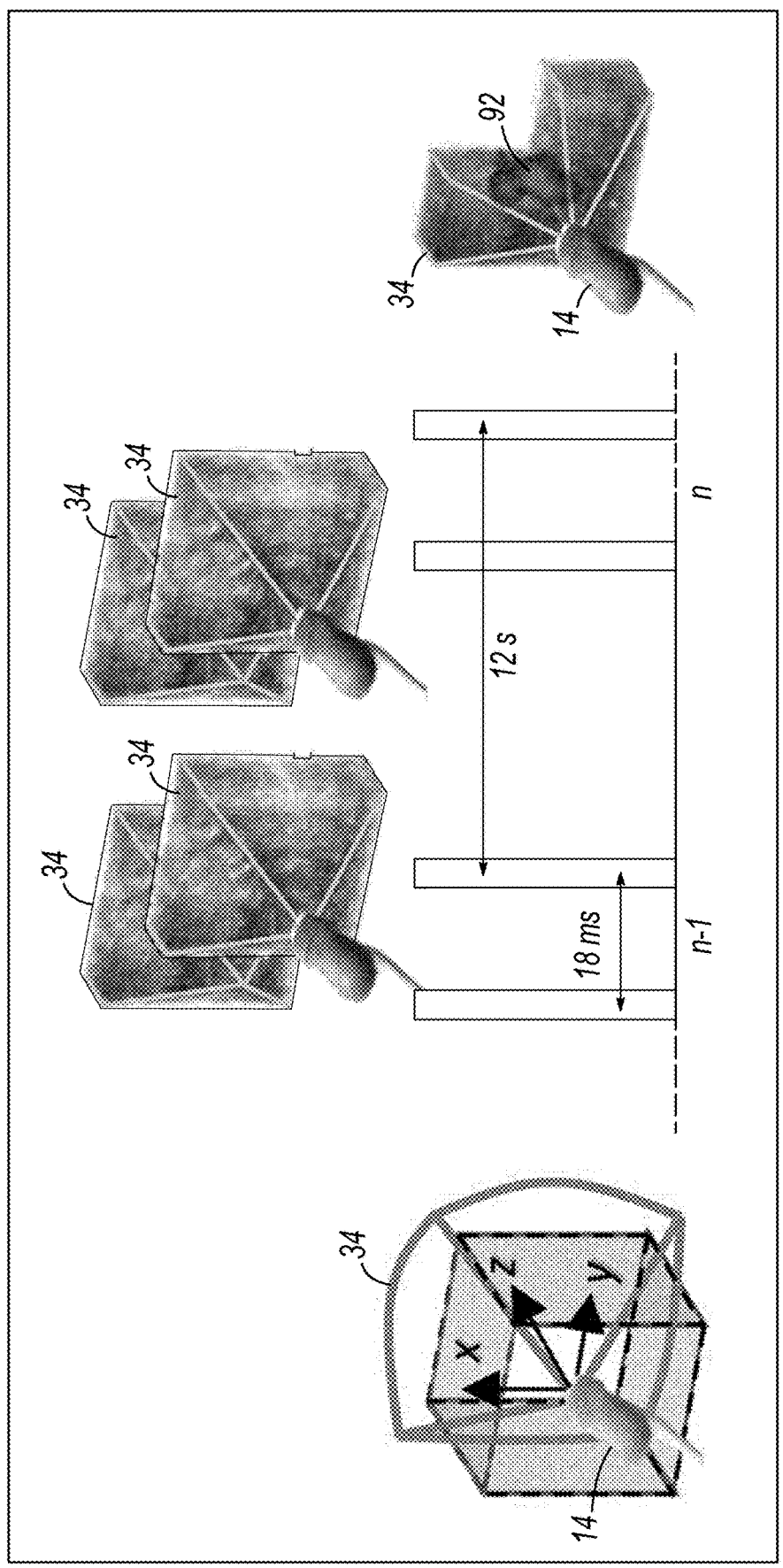
FIG. 6 is a diagrammatic view showing the capture of a plurality of pulse-echo image volumes of the tissue sample of FIG. 4.

FIG. 6 depicts pairs of sequential pulse-echo image volumes 34 illustrative of those acquired and stored by the ultrasound scanner 12. For three-dimensional pulse-echo imaging of tissue during radiofrequency ablation, the imaging probe 14 included a 4Z1c matrix array transducer, and the ultrasound scanner 12 was an Acuson SC2000 scanner, both of which may be obtained from Siemens AG of Erlangen, Germany. The 4Z1c includes a clinical matrix ultrasound phased array having 48×36 elements, an active aperture of 19.2×14.4=276.5 mm$^2$, and a bandwidth 1.5-3.5 MHz. The ultrasound scanner 12 was set to a center frequency of 2.8 MHz, an imaging depth 110 mm, and a frame rate of 55 volumes per second. Throughout each ablation experiment, pairs of sequential pulse-echo image volumes 34 were acquired with an inter-frame time τ=18 ms. The pulse-echo image volumes 34 were stored by the ultrasound scanner 12, with one pulse-echo image volume pair being stored approximately every 12 seconds. Each pulse-echo image volume 34 comprised a 79°×79° pyramid having 55×54 demodulated complex x-y scan lines. Each scan line had a length 376 of samples and sampling rate 2.5 MHz. For each pulse-echo image volume pair, the ablation zone 92 was within the pyramidal pulse-echo image volume 34.

Image data was processed using MATLAB, which is a software program available from MathWorks of Natick, MA. Scan conversion from the scanner's pyramidal (i.e., frustum) coordinate system to a three-dimensional Cartesian coordinate system was performed using the known positioning of scan lines. As confirmed with the manufacturer, scan lines were spaced in equal increments of sin(θ) and sin(φ) in the azimuth and elevation directions. Corresponding relations between the pyramidal coordinates (r, θ, φ) and Cartesian coordinates (x, y, z) are given by Equations 1-3 above.

For scan conversion, the coordinates of each sample were first determined in the pyramidal coordinate system. A Cartesian grid with isotropic step size of one millimeter was then defined and the pyramidal coordinates of each grid point were determined. The sampled volumes of complex echo data were then scan-converted onto the Cartesian grid using trilinear interpolation within the pyramidal coordinate system.

For monitoring the thermal ablation process in three dimensions, echo decorrelation imaging was extended to three dimensions. All computations of echo decorrelation and integrated backscatter maps were performed within a spherical region of interest with a 40 mm diameter (corresponding to the targeted ablation zone diameter of 20 mm plus a 10 mm radial margin), centered at the known position of the tip 28 of ablation probe 18. This computation starts with zero-lag, spatially windowed cross-correlation between sequential complex pulse-echo image volumes $I_0$ and $I_1$, as shown below, $$R_{01}(r;n) = \langle I_0(r;n)^* I_1(r;n) \rangle = \iiint w(r-r') I_0(r';n)^* I_1(r';n) dV' \quad \text{Eqn. 22}$$

$$w(r) = e^{-r^2/2\sigma^2} \quad \text{Eqn. 23}$$

where temporal indices n sequentially number each acquired pulse-echo image volume pair, r is the position vector within a pulse-echo image volume, $I_0(r)^*$ is the complex conjugate of pulse-echo image volume $I_0$, and dV' is a differential volume element corresponding to the vector integration variable r'. In the following, angle brackets denote the same operation of convolution with a Gaussian window with width parameter σ. Choice of the width parameter σ specifies the size of the three-dimensional correlation window employed (e.g., a full width at half maximum (FWHM) =2.355×σ), so that larger σ values reduce spatial resolution of echo decorrelation image volumes but increase averaging of spatially random variations.

Corresponding zero-lag, spatially windowed autocorrelations of complex pulse-echo image volumes can be defined as:

$$R_{00}(r,n) = \langle |I_0(r,n)|^2 \rangle, R_{11}(r,n) = \langle |I_1(r,n)|^2 \rangle \quad \text{Eqn. 24}$$

$$\beta^2(r,n) = R_{00}(r,n) R_{11}(r,n) \quad \text{Eqn. 25}$$

Locally normalized echo decorrelation is then given as a normalized correlation coefficient subtracted from unity, with the result divided by inter-frame time τ, $$\Delta_L(r, n) = \frac{1}{\tau}\left(1 - \frac{|R_{01}(r, n)|^2}{\beta^2(r, n)}\right) = \frac{\beta^2(r, n) - |R_{01}(r, n)|^2}{\tau[\beta^2(r, n)]} \quad \text{Eqn. 26}$$

This definition of decorrelation may relate echo decorrelation to decoherence of the scattering medium reflectivity. Normalization by the inter-frame time τ accounts for observed increases in echo decorrelation versus temporal lag, consistent with expected continuous heat-induced changes in tissue structure.

Since echo decorrelation as defined by Equation 26 can become large due to electronic noise within hypoechoic regions, a globally normalized echo decorrelation can also be defined, normalized by a spatial mean of the autocorrelation product within the imaged region of interest, as follows:

$$\Delta_G(r, n) = \frac{\beta^2(r, n) - |R_{01}(r, n)|^2}{\tau[\overline{\beta^2}(n)]} \quad \text{Eqn. 27}$$

Echo decorrelation as defined by Equation 27 tends to be larger in regions with greater tissue reflectivity. As a compromise between artifacts associated with tissue echogenicity in the definitions provided by Equations 26 and 27, a combined echo decorrelation parameter is defined below, which is essentially Equation 10 with the further inclusion of temporal index n, $$\Delta_c(r, n) = \Delta(r, n) = 2\left[\frac{\beta^2(r, n) - |R_{01}(r, n)|^2}{\tau[\beta^2(r, n) + \overline{\beta^2}(n)]}\right] \quad \text{Eqn. 28}$$

By any of these definitions, echo decorrelation represents local deviations between a pair of complex pulse-echo image volumes 34 per inter-frame time τ. The resulting echo decorrelation image volumes are zero in regions with no change in pulse-echo image data and maximum in regions where local echo changes are greatest. To track all measured changes in pulse-echo image volumes, cumulative echo decorrelation is defined as the temporal maximum decorrelation at each position r, for each of the definitions provided by Equations 26-28.

For comparison, relative integrated backscatter (IBS) images were defined as the decibel-scaled ratio between the square root of the image autocorrelation product, β(r,n) at the current and first recorded image volume pairs:

$$IBS(r, n) = 10 \times \log_{10}\left(\frac{\beta(r, n)}{\beta(r, 1)}\right) \quad \text{Eqn. 29}$$

Thus, mapping increases in local echogenicity relative to the tissue before radiofrequency ablation. Integrated backscatter images were computed from the same pulse-echo image data and accumulated in the same manner as the echo decorrelation image volumes.

B-Mode images were constructed from logarithmically scaled envelopes $10 \times \log_{10}[|I_1(r)|]$ of the in-phase/quadrature scan lines and displayed using a 65 dB dynamic range. For displaying decorrelation and integrated backscatter maps, duplex B-mode/echo decorrelation and B-mode/integrated backscatter images were constructed by overlaying the grayscale B-mode image with a pseudocolor image of the $\log_{10}$-scaled echo decorrelation per millisecond or the decibel-scaled integrated backscatter, respectively. Transparency of the echo decorrelation and integrated backscatter overlays was proportional to the logarithmically scaled parameters mapped over a defined dynamic range.

For direct comparison of three-dimensional echo decorrelation and integrated backscatter images with ablated tissue histology, receiver operating characteristics curve analysis was utilized. Segmented maps of ablated tissue across all 14 trials were compared voxel-by-voxel with measured echo decorrelation and integrated backscatter parameters within a spherical region of interest 26 defined by a 20 mm radius centered at the tip 28 of ablation probe 18. This choice of region of interest 26 included both the targeted ablation zone 92 of radius 10 mm and an additional 10 mm margin, beyond which the tissue was assumed to be unablated. Receiver operating characteristics curves plot true-positive ratio versus false-positive ratio for prediction of local ablation as a parametric function of the parameter threshold. The area under the receiver operating characteristics curve (referred to herein as the AUC) is 1.0 for perfect prediction of all ablated voxels and 0.5 for prediction equivalent to chance. Optimal thresholds for ablation prediction for all predictors were defined as those corresponding to the point nearest the top left-hand corner of the receiver operating characteristics plot, simultaneously maximizing the sensitivity and specificity of the predictor.

To optimize ablation prediction with respect to trade-offs between spatial resolution and stochastic averaging, the AUC for the combined echo decorrelation as defined by Equation 28 was computed as a function of the correlation window width parameter σ over the range 1-8 mm. The maximum prediction curve was obtained for σ=3 mm, and this value of σ was used in all subsequent analysis. Notably, the AUC for combined echo decorrelation was insensitive to the choice of this parameter, such that the difference between minimum and maximum AUC was about 0.04 over the investigated range.

Using MATLAB, AUC values were compared to the null hypothesis (AUC=0.5) and the statistical significance was calculated by a one-tailed Z test employing a general model for the AUC standard error (one-tailed, significance criterion $p<0.05$). The statistical significance of differences between AUC values for all normalizations of echo decorrelation and integrated backscatter was calculated using "R" (which is a free environment for statistical computing and graphics available from the R Foundation for Statistical Computing, Vienna, Austria) and the method of DeLong (two-tailed paired tests, significance criterion p<0.05). The method of DeLong is disclosed in detail by the article entitled "Comparing the areas under two or more correlated receiver operating characteristic curves: A nonparametric approach," by E. R. DeLong, D. M. DeLong, and D. L. Clarke-Pearson, Biometrics 44(3), pp. 837-845 (1988).

For assessments of statistical significance, an effective number of independent ablation predictions $N_{eff}$ was determined from the total number of predicted voxels $N_{total}$ and the maximum hexagonal packing density of spheres with diameter $d=2.355 \times \sigma$, resulting in, $$N_{eff} = \sqrt{2}(l/d)^3 N_{total} \qquad \text{Eqn. 30}$$

where $l=1$ mm is the isotropic step size of the Cartesian grid employed. To account for this estimated number of independent predictions, Z statistics were scaled by the factor $(N_{eff}/N_{total})^{1/2}$ and effective p values (significance criterion p<0.05, two-tailed) were determined using the cumulative distribution function of the standard normal distribution.

To assess the dependence of echo decorrelation and integrated backscatter parameters on local tissue temperature, measurements from the four thermocouples integrated into the ablation probe 18 were correlated with echo decorrelation and integrated backscatter values at the known thermocouple positions. This temperature dependence was visualized using histogram plots of predictor values versus co-located measured temperature and quantified by linear regression between logarithmically scaled predictors and local temperature. The statistical significance of predictor-temperature relationships was assessed based on the cumulative distribution function of the Pearson correlation coefficient r.

The potential utility of these imaging methods for predicting ablation zone margins and volumes was assessed using weighted K-means clustering. This approach was designed to provide an unsupervised segmentation of ablation zones 92 based on objective data, while incorporating a priori knowledge that tissue nearer the tip 28 of ablation probe 18 is more likely to be ablated. Voxels within the 20 mm radius computational region of interest 26 centered at the tip 28 of ablation probe 18 were characterized by two features for each image-based predictor. The first feature was the logarithmically scaled predictor ($\log_{10}$-scaled decorrelation/ms or integrated backscatter) and the second feature was the Euclidean distance r from the tip 28 of ablation probe 18, across all trials. Each feature was scaled using linear min-max normalization, such that scaled values ranged between 0 and 1. Clustering in this two-dimensional feature space was then performed for K=2 clusters, with the inner cluster (smaller distance from the tip 28 of ablation probe 18) classified as ablated and the outer cluster classified as unablated.

To initiate the K-means iteration, centroids for the two clusters were initialized as points within the feature space considered most and least likely to be ablated, respectively. The initial centroid for the ablated cluster was placed with the first feature at the maximum predictor value within a small spherical region around the tip 28 of ablation probe 18 ($r \leq 0.2$ mm) and the second feature at a normalized Euclidean distance of 0. The initial centroid for the unablated cluster was chosen with the first feature at the minimum predictor value within the spherical shell $19.8 \leq r \leq 20$ mm and the second feature at a normalized Euclidean distance of 1.

To iteratively update the two clusters, Euclidean distances from the two centroids were computed for all points within the two-dimensional feature space, and data points assigned to their nearer centroid. The two centroids were then updated within each respective cluster to place the first feature at its mean value and the second feature at its mean value multiplied by a weight w. This weight was configured to account for the skewness of the second feature, i.e., the much higher prevalence of voxels at higher distances from the tip 28 of ablation probe 18. These iterations were repeated until the average volume prediction error across all trials was less than 10%, up to a maximum of 15 iterations.

Predicted ablation zone volumes, defined as the summed volume of all voxels within the ablated cluster, were compared to measured ablation zone volumes for each experiment (N=1 to 14). To find an appropriate weight to minimize the volume prediction error, the clustering process was repeated for a vector of weights $0.4 \leq w \leq 1$ with a step size of 0.05, and the RMS error of volume prediction was assessed across all 14 trials. For the final choice of weight w, RMS error in milliliters, normalized RMS error (expressed as a percentage of RMS measured volume), and correlation coefficients of predicted versus measured volumes were computed.

To assess agreement of predicted and measured ablation zone margins, Dice coefficients were computed between the ablation zones 92 segmented manually from scanned tissue sections and those predicted by weighted K-means clustering of predictor values and distances from the tip 28 of ablation probe 18. Dice coefficients were compared between predictors using two-tailed, paired Student t tests with the significance criterion $p \leq 0.05$.

Figure 7:
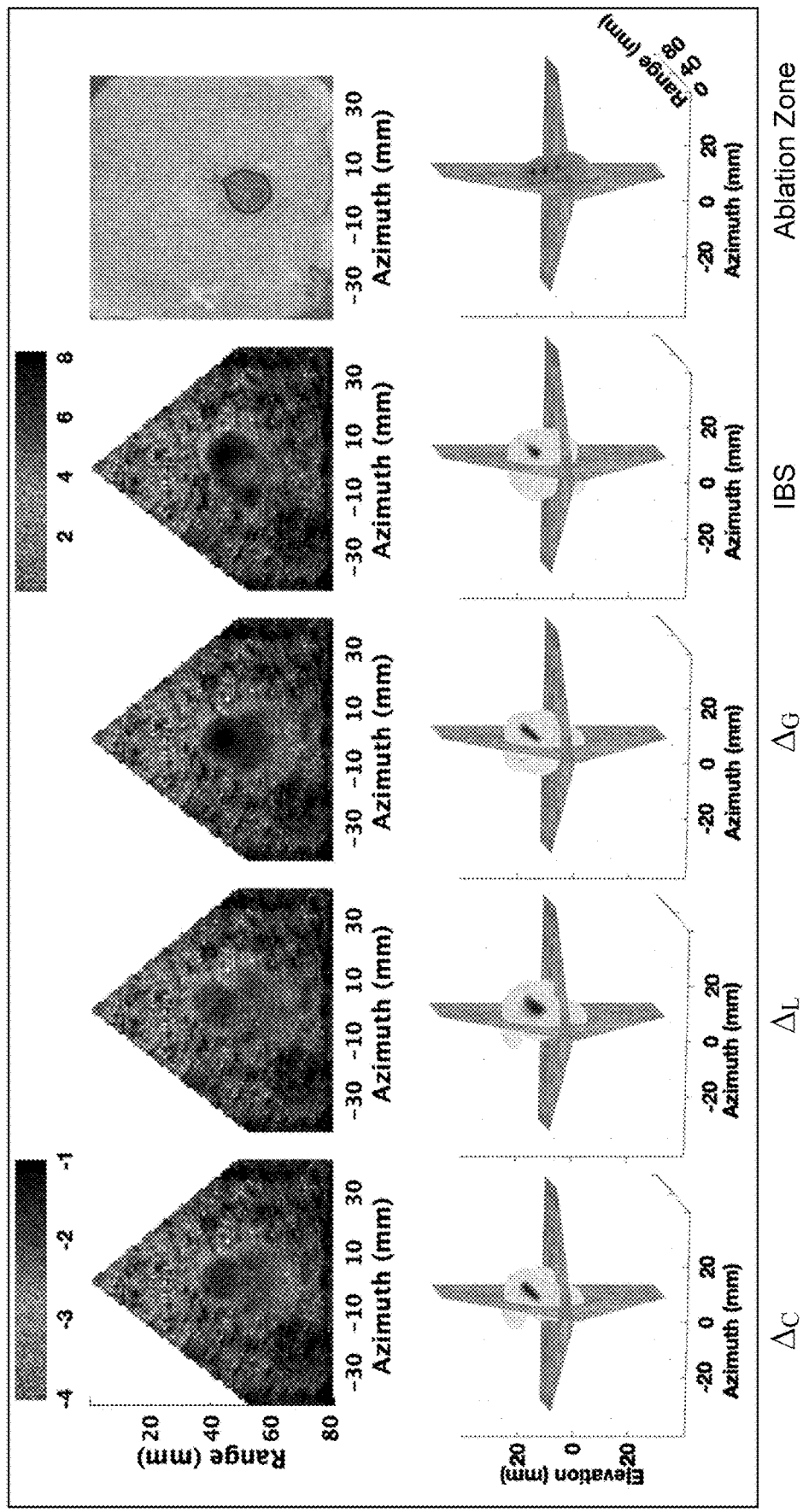
FIGS. 7 and 8 are graphical views of three-dimensional echo decorrelation and integrated backscatter images with corresponding ablated tissue histology for exemplary ablations of two ablated tissue samples of FIG. 5.
Figure 8:
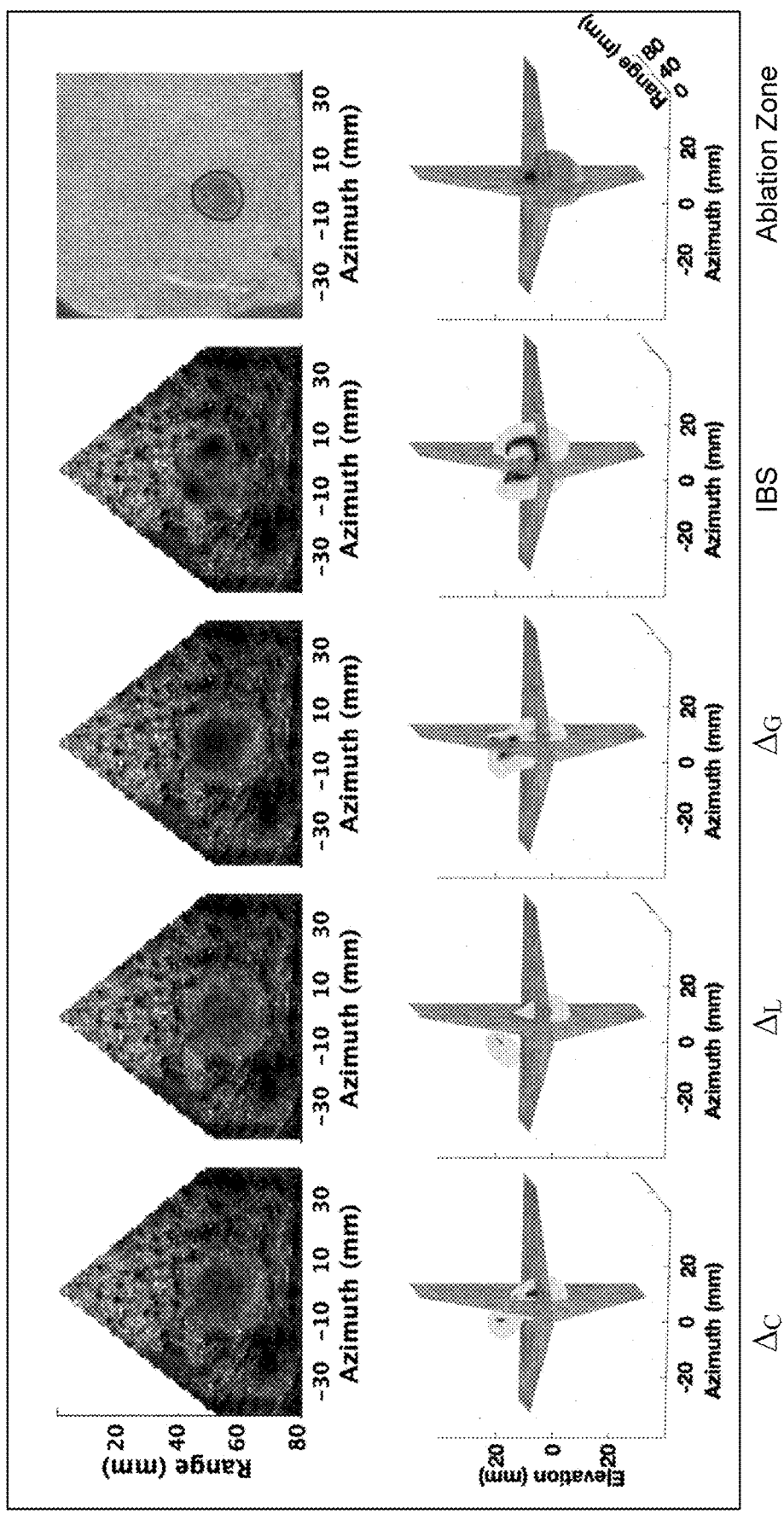

FIGS. 7 and 8 depict three-dimensional echo decorrelation and integrated backscatter images, respectively, with corresponding ablated tissue histology for two representative trials. The first row of each panel shows parametric images of combined echo decorrelation, locally and globally normalized echo decorrelation, and integrated backscatter superimposed on corresponding cross-sections of the B-mode image volume as well as an optically scanned and segmented section of the ablated tissue volume, all at the elevation position nearest the tip 28 of ablation probe 18. Inner boundaries of the sample container are visible in the B-mode images as bright borders around the pulse-echo image volume. The second row of each panel shows isosurface renderings of the same parameters and the ablated tissue volume with corresponding perpendicular cross-sections of the pyramidal B-mode image volume. Decorrelation isosurfaces are plotted at the value $10^{-3.0}$/ms, while integrated backscatter isosurfaces are plotted at the value 4.0 dB.

The parametric images, as well as their isosurface renderings generally correspond well with the ablation zones 92 seen in the corresponding tissue sections and isosurface renderings of the segmented three-dimensional ablation zone 92. The best correspondence is seen for globally normalized echo decorrelation as defined by Equation 27, which generally shows high values in voxels where ablation occurred. Locally normalized and combined echo decorrelation image volumes as defined by Equations 26 and 28, respectively, were also consistent with the corresponding ablated tissue histology. However, integrated backscatter maps defined by Equation 29 were less consistent, showing some low values within observed ablation zones 92. General correspondence can be seen between echo decorrelation image volumes and the ablation zone 92.

Figure 9:
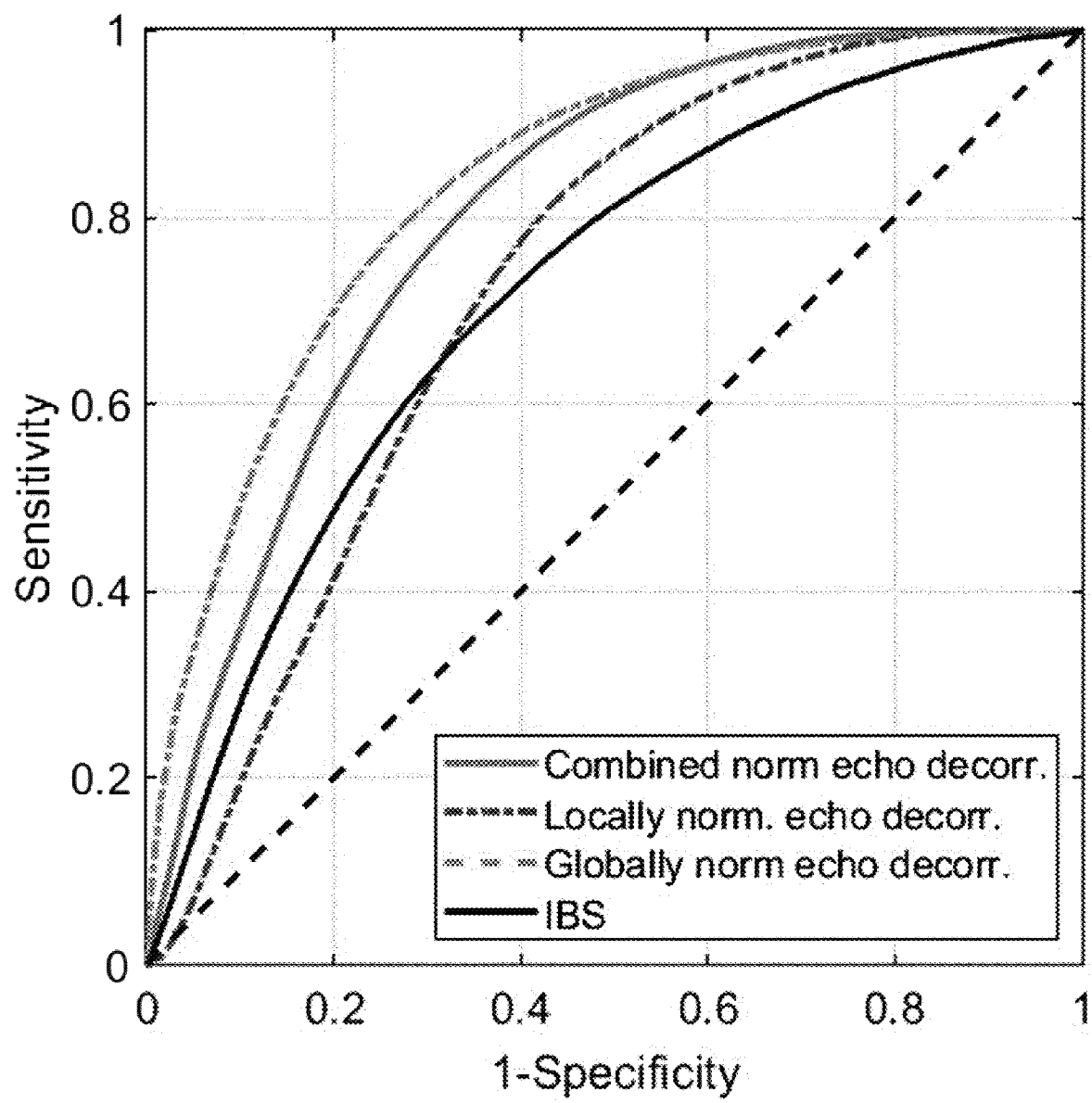
FIG. 9 is a graphical view including plots that show results of receiver operating characteristics curve analysis and predicted results of ablation by echo decorrelation imaging and by integrated backscatter imaging for ablation tests performed using the test environment of FIG. 4.

FIG. 9 and Table I show the results of receiver operating characteristics curve analysis, as well as the results from assessing prediction of local ablation by echo decorrelation imaging and by integrated backscatter imaging. All four image parameters predicted local ablation significantly better than chance ($p<10^{-16}$). Globally normalized echo decorrelation showed the highest predictive capability (AUC=0.837), while integrated backscatter showed the lowest predictive capability (AUC=0.719). The AUC for locally normalized echo decorrelation was statistically equivalent to integrated backscatter (p=0.704). All other AUC values were significantly different from one another ($p<10^{-5}$), with prediction performance of combined echo decorrelation (AUC=0.801) falling between locally and globally normalized decorrelation. Optimal thresholds for prediction of local ablation were similar for the three definitions of echo decorrelation investigated, ranging from −3.71 to −3.57 ($\log_{10}\Delta$/ms).

The minimum average volume prediction error, computed across all trials and all four predictors, was near zero for w=0.8 and was <0.5 ml for 0.7≤w≤0.9. All further analysis employed a weight w=0.8.

Figure 13:
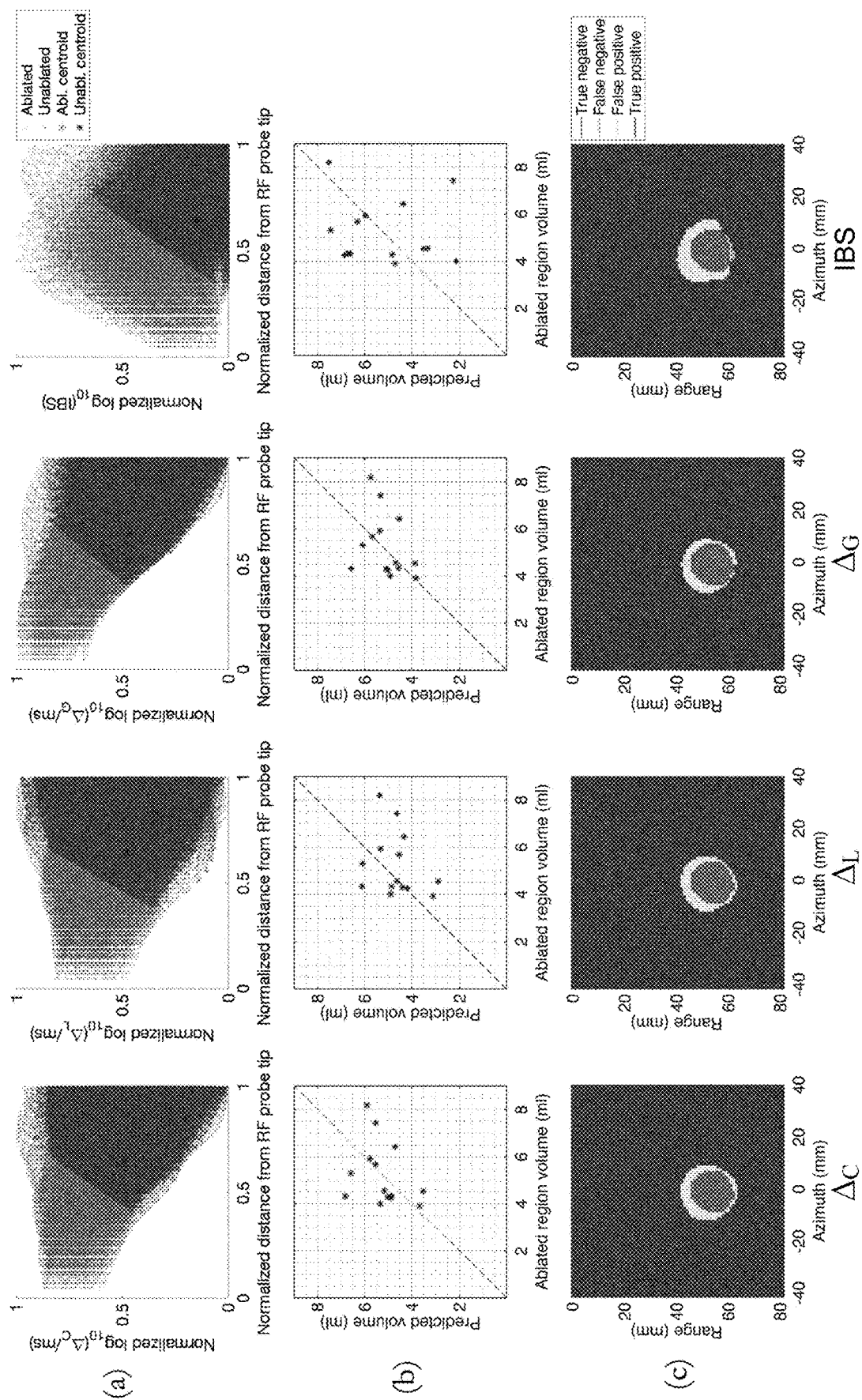
FIG. 13 is a graphical view of scatter plots of final clusters classified as ablated and unablated with their respective centroids for each predictor and predicted versus measured ablation zone volumes, and cross-sections of predicted and measured ablation zones.

FIG. 13 shows scatter plots of the final clusters classified as ablated and unablated with their respective centroids across all 14 trials for each predictor, scatter plots of predicted versus measured ablation zone volumes across all 14 trials, and cross-sections of predicted and measured ablation zones 92 for the same trials and planes illustrated in FIGS. 7 and 8.

Table II summarizes statistical results for the unsupervised prediction of ablation zones 92 by weighted K-means clustering. Absolute and normalized RMS errors of predicted volumes ranged from 1.27 ml (23.5%) for globally normalized echo decorrelation to 2.09 ml (38.9%) for IBS. Correlation coefficients between predicted and measured ablation zone volumes across all trials (N=1 to 14) were

TABLE I

| Prediction Parameter | AUC | Optimal Threshold | p value vs. AUC = 0.5 | p value vs. $\Delta_L$ | p value vs. $\Delta_G$ | p value vs. IBS |
|---|---|---|---|---|---|---|
| $\Delta_C$ | 0.801 | −3.71[$\log_{10}\Delta$/ms] | $<10^{-16}$ | $<10^{-16}$ | $2.42 \times 10^{-11}$ | $3.02 \times 10^{-6}$ |
| $\Delta_L$ | 0.726 | −3.66[$\log_{10}\Delta$/ms] | $<10^{-16}$ | | $<10^{-16}$ | 0.704 |
| $\Delta_G$ | 0.837 | −3.57[$\log_{10}\Delta$/ms] | $<10^{-16}$ | | | $4.04 \times 10^{-13}$ |
| IBS | 0.719 | 2.64 dB | $<10^{-16}$ | | | |

Figure 10:
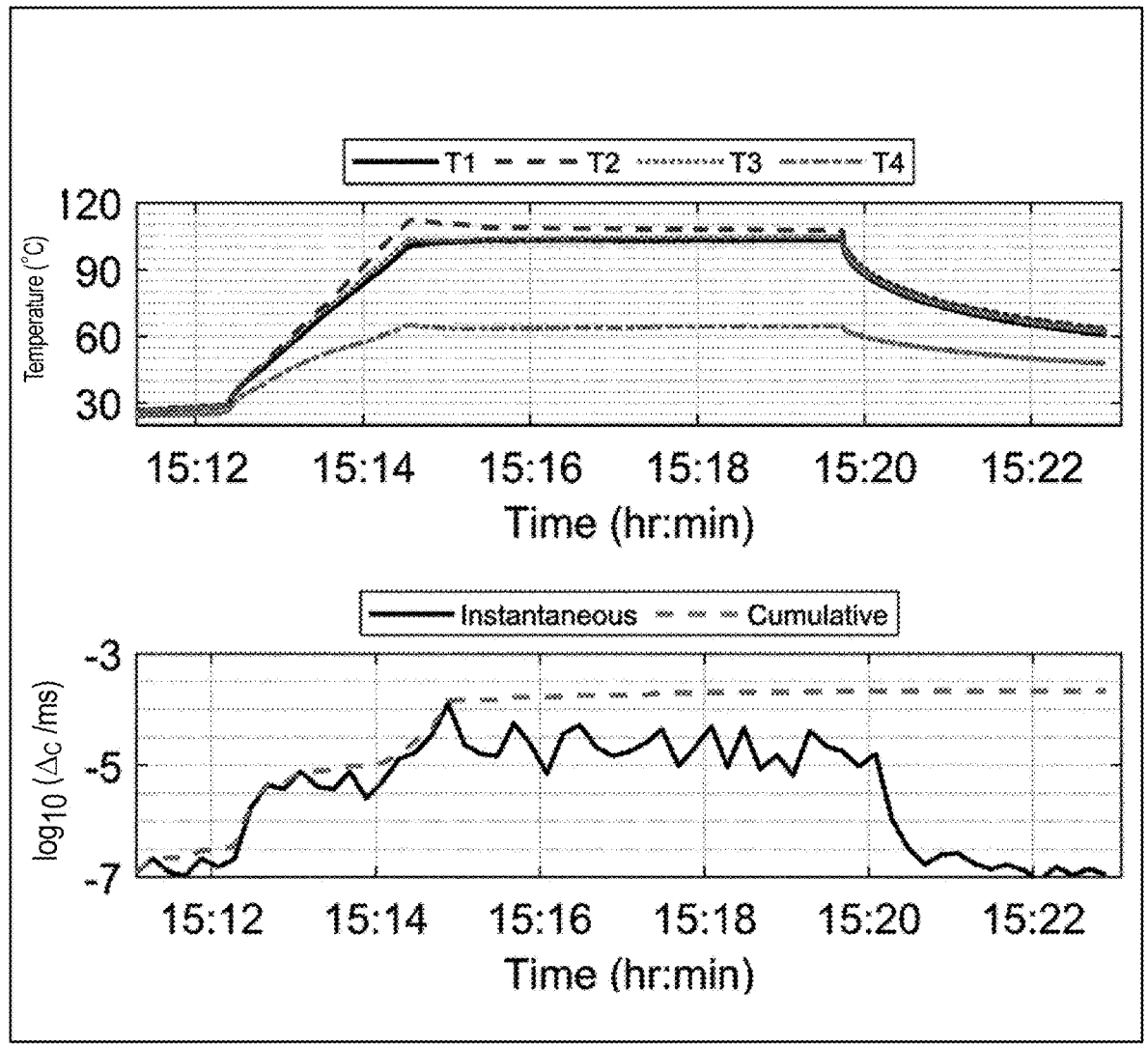
FIGS. 10 and 11 are graphical views including plots of temperature, instantaneous echo decorrelation, and cumulative combined echo decorrelation averaged within a region of interest of exemplary tissue samples of FIG. 4.
Figure 11:
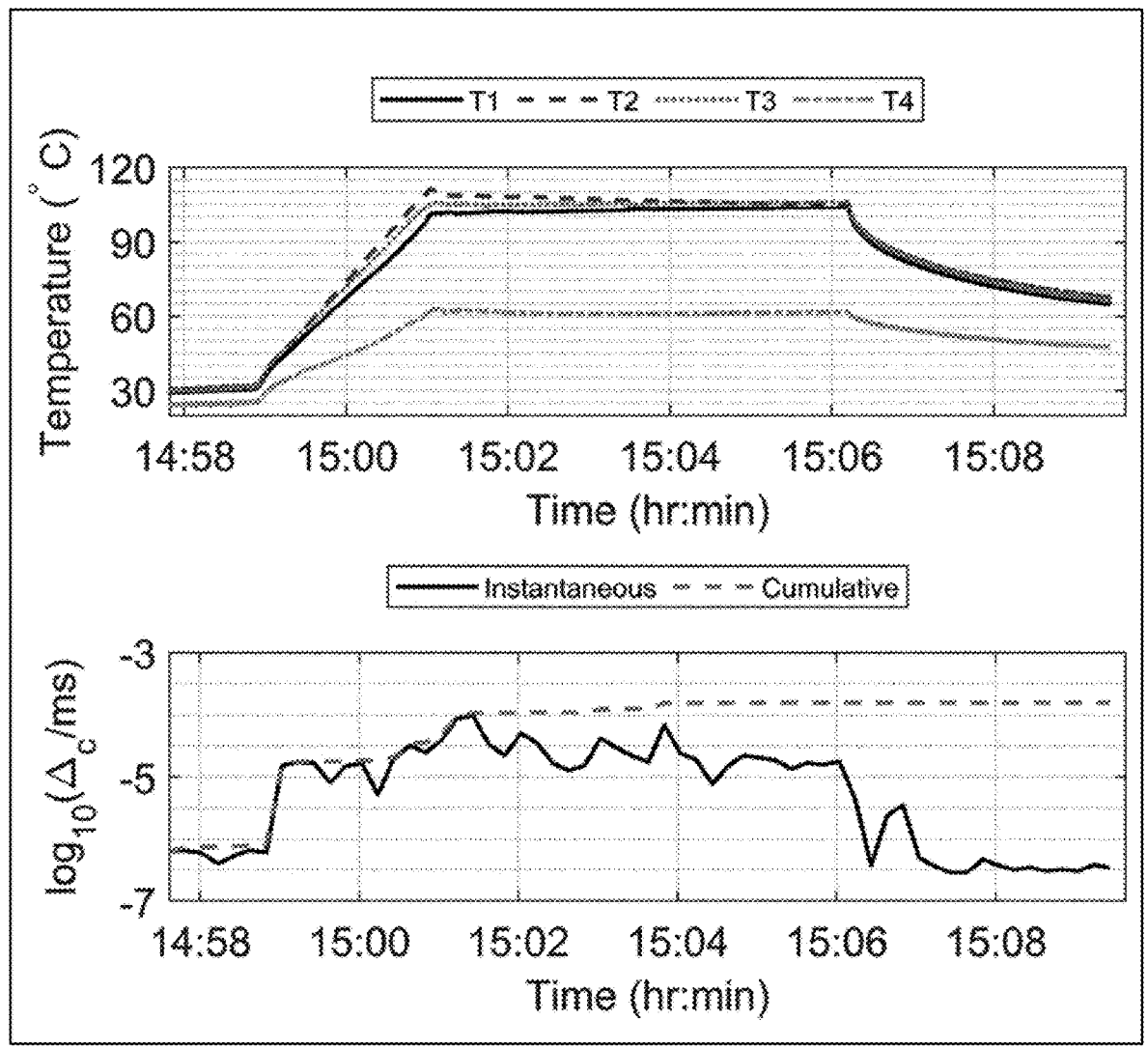

FIGS. 10 and 11 depict graphs including plots of temperatures from four thermocouples integrated into the ablation probe 18, together with simultaneous instantaneous echo decorrelation and cumulative combined echo decorrelation averaged within the computational region of interest. Thermocouples T1, T2, and T3 were located at the nominal boundary of the expected ablation zone 92 (10 mm from the ablation probe axis for a probe deployment of 20 mm diameter), while T4 was located outside the expected ablation zone 92, 15 mm below the tip 28 of ablation probe 18 in the elevation direction. Thus, T4 generally measured a lower temperature than the other three thermocouples. During about the first two minutes of radiofrequency ablation treatment, tissue temperature and echo decorrelation tended to increase together. After the radiofrequency generator held tissue at the set target temperature of 105° C. (about 2-7 min of treatment), instantaneous and cumulative echo decorrelation parameters tended to stabilize. After completion of radiofrequency ablation treatment (about 7-9.5 min), the instantaneous echo decorrelation tended to decline.

Figure 12:
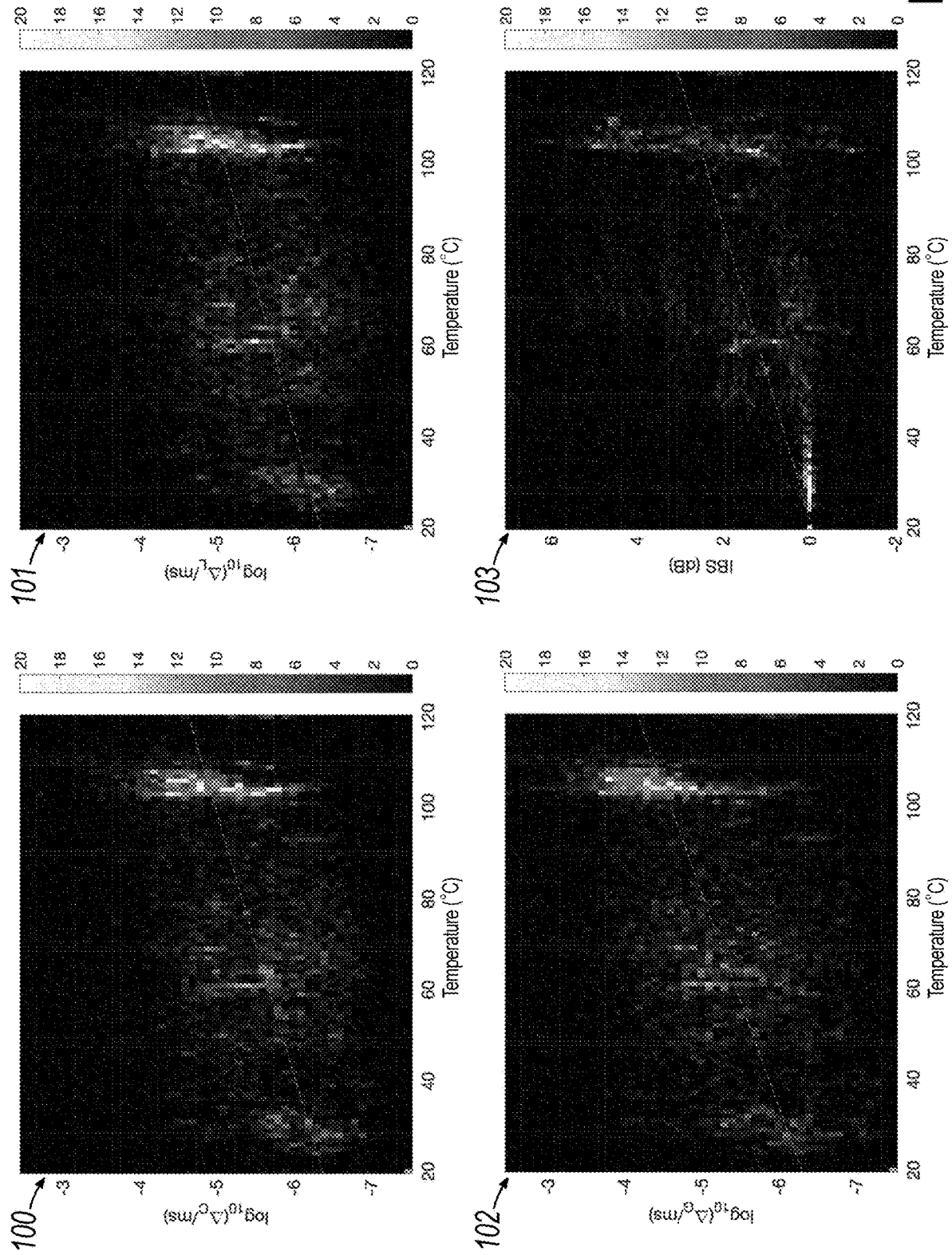
FIG. 12 is a graphical view of two-dimensional histogram plots of four ablation predictors versus time-dependent measured temperature for ablation tests performed using the test environment of FIG. 4.

FIG. 12 depicts two-dimensional histogram plots 100-103 of instantaneous measured values for all four predictors versus time-dependent measured temperature, evaluated at the positions of the four integrated thermocouples at all time points within all 14 ablation trials. Also shown as superimposed dashed lines are the lines of best fit for $\log_{10}$-scaled echo decorrelation and dB-scaled integrated backscatter versus temperature, computed by linear regression. All four predictors were significantly but weakly correlated with tissue temperature ($p<10^{-15}$, N=3360). The correlation coefficient between local predictors and local temperature was smallest for locally normalized echo decorrelation (0.435) and largest for globally normalized echo decorrelation (0.519).

For prediction of ablation zone volumes using the weighted K-means clustering approach, optimal weights w typically fell within the range 0.7≤w≤0.9 for all four predictors, with results not highly sensitive to the weight value.

positive but not statistically significant for all predictors, and were substantially greater for the echo decorrelation parameters (0.269-0.333) than for integrated backscatter (0.110). Mean Dice coefficients between predicted and measured ablation zones 92 were similar for the three echo decorrelation parameters (0.662-0.676), but substantially higher for integrated backscatter (0.597), a statistically significant difference ($p<10^{-3}$). The only statistically significant difference between Dice coefficients for the echo decorrelation predictors was a marginally higher coefficient for combined decorrelation, compared to globally normalized decorrelation (p=0.0165).

TABLE II

| Prediction Parameter | RMS Volume Error | Normalized RMS Volume Error | Correlation Coefficient r | Dice Coefficient (mean ± std. dev.) |
|---|---|---|---|---|
| $\Delta_C$ | 1.31 | 24.3% | 0.323 | 0.676 ± 0.0882 |
| $\Delta_L$ | 1.41 | 27.3% | 0.269 | 0.670 ± 0.0852 |
| $\Delta_G$ | 1.27 | 23.5% | 0.333 | 0.662 ± 0.0998 |
| IBS | 2.09 | 38.9% | 0.110 | 0.597 ± 0.1250 |

The present disclosure shows the usefulness of three-dimensional echo decorrelation imaging for monitoring clinical radiofrequency ablation of the liver, as well as similar bulk ablation approaches such as microwave ablation. All investigated image parameters predict local ablation significantly better than chance, as assessed by receiver operating characteristics curve analysis ($p<10^{-16}$). For locally normalized, globally normalized, and combined three-dimensional echo decorrelation, AUC covered the range 0.726-0.837.

Notably, AUC for ablation prediction using echo decorrelation was relatively high, even though echo decorrelation image volumes were acquired only once every 11 seconds and scan line density was relatively low, e.g., 55×54 scan lines as compared to two-dimensional B-mode imaging with over 100 scan lines in a single plane. The results suggest that alternative normalizations may also be appropriate for monitoring of radiofrequency ablation. Globally normalized echo decorrelation, defined by Equation 27 to incorporate normalization by spatially averaged echo autocorrelation, showed the best predictive ability among the four predictors considered (AUC=0.837, $p<10^{-12}$ versus combined echo decorrelation). Globally normalized echo decorrelation also showed the best qualitative correspondence with local tissue ablation, as seen in FIGS. 7 and 8, where this parameter corresponds more closely with observed ablation zones 92 than the other three predictors. However, the three echo decorrelation normalizations investigated resulted in similar monitoring performance in some respects. Optimal thresholds for local ablation prediction, corresponding to the point on each receiver operating characteristics curve nearest the top left corner, were close for all three decorrelation parameters, as seen in Table I.

Correlation coefficients between instantaneous parameter values and local tissue temperature were higher for globally normalized echo decorrelation (0.519) than for other predictors (0.435-0.502). Relations between each predictor and local temperature were statistically significant but weak, as seen in FIG. 12. This suggests that three-dimensional echo decorrelation and integrated backscatter are not direct predictors of local temperature.

Similarly, comparisons between measured ablation zone volumes and those predicted by weighted K-means segmentation were similar for all three echo decorrelation normalizations (normalized RMS errors 23.5%-27.3%), all of which showed better prediction of ablation volumes compared to integrated backscatter (normalized RMS error 38.7%). Dice coefficients between predicted and measured ablation zones 92 had means between 0.662 and 0.676 for the echo decorrelation predictors, indicating substantial agreement, and a mean±standard deviation 0.597±0.125 for integrated backscatter, indicating moderate to substantial agreement. More sophisticated prediction approaches (e.g., employing machine-learning techniques) could result in more accurate estimation of total ablated volume and ablation zone margins from measured echo decorrelation or integrated backscatter data.

Sources of uncertainty in these measurements included imprecision of the method employed for tissue sectioning. Since ablated tissue was sectioned with a section thickness of 3-4 mm, the resulting reconstructed three-dimensional ablation zone 92 was coarsely sampled in the elevation direction. This resulted in uncertainty in estimating the position of the tip 28 of ablation probe 18, potentially causing registration error along the elevation direction. Some misalignments likely resulted between echo decorrelation image volumes, three-dimensional integrated backscatter maps, and corresponding tissue sections. In addition, since the ablation zone volume is measured after freezing of tissue, some error may be caused by the expansion tissue surrounding the ablation zone 92, changing the shape of the ablation zone 92 to some extent. Use of finer sectioning or three-dimensional interpolation of the mapped ablation zones may result in better correspondence between predicted and measured ablation, and thus higher AUC values for all predictors. In addition, assessment of the ablation zone 92 from ablated tissue histology may be limited because the tissue can contract as it loses water during thermal ablation.

Another source of uncertainty during ultrasound imaging of in vivo and clinical thermal ablation is tissue motion due to respiration. To mitigate motion-induced decorrelation, pulse-echo image volumes can potentially be acquired at specific time points during the breathing cycle, for example at the end of the exhale phase, either manually or by automatic gating. Motion effects can also be compensated by separate measurements of motion-induced decorrelation. Notably, integrated backscatter may be less sensitive to motion due to its dependence on echo amplitude rather than echo waveforms, potentially making it more suitable for imaging during respiration. Although the predictive capability of integrated backscatter (AUC=0.719) was inferior to globally normalized echo decorrelation imaging (AUC=0.837), this potential insensitivity to motion may be useful in clinical practice.

During clinical radiofrequency ablation treatment, thermal coagulative necrosis is typically targeted to a region enclosing an entire tumor plus a tissue margin. To avoid overtreatment (potentially damaging major liver structures such as the hepatic artery) or undertreatment (potentially resulting in cancer recurrence), monitoring ablation progress in three dimensions is desirable. Implementation of echo decorrelation imaging as a built-in feature on clinical ultrasound scanners, with computational cost comparable to color and power Doppler imaging, would enable true real-time echo decorrelation imaging, e.g., with volumetric frame rates>10 Hz. The resulting improvements in temporal resolution of echo decorrelation imaging may further increase its ability to predict local ablation and over-all ablation progress. Although echo decorrelation imaging only provides real-time feedback during the ablation process, additional ultrasound imaging methods, such as elastography or contrast-enhanced imaging, could also be employed using the same scanning system to assess and quantify the ablation zone 92 after treatment is complete.

To reduce dependence of treatment outcomes on operator skill and to increase the precision of these procedures, automatic control of thermal ablation procedures may be used. In one approach for controlling radiofrequency ablation using echo decorrelation imaging, a predictor value may be measured at each voxel inside a region of interest and either its minimum or average value used as the treatment end point. Optimal thresholds from receiver operating characteristics curve analysis in this study can be potentially used as endpoints for control of the tumor ablation. To confirm local ablation of malignant tissue and avoid recurrence, it may be appropriate to choose thresholds corresponding to higher specificity of local ablation prediction. For example, treatments may be stopped when the minimum echo decorrelation inside a control region of interest reaches a specific threshold chosen for a predetermined specificity (e.g., 90%) and a predetermined sensitivity (e.g., 83%) of local ablation prediction based on receiver operating characteristics curve analysis.

EXPERIMENTAL RESULTS—EX VIVO HUMAN LIVER

As described above, echo decorrelation imaging can be used to predict local thermal ablation and control ablation in animal liver and tumor tissue, both ex vivo and in vivo. As a further demonstration of this monitoring and control approach to clinical liver tumor ablation, the below experimental results describe control of radiofrequency ablation in ex vivo human liver tissue using three-dimensional echo decorrelation imaging.

Experimental data was obtained by ablating human liver tissue, including postmortem normal liver as well as explanted cirrhotic and fatty liver. During ablation, three-dimensional echo decorrelation image volumes were constructed from paired sequential pulse-echo image volumes.

For controlled radiofrequency ablation trials, ablation was ceased automatically after a cumulative echo decorrelation that was spatially averaged within a spherical region of interest matching the planned ablation zone exceeded a predetermined threshold. This control algorithm was tested in N=6 controlled ablation trials, of which five trials attained the predetermined decorrelation threshold. Three-dimensional echo decorrelation image volumes were compared to segmented ablation zones, using receiver operating characteristic curve analysis. To assess the effect of image-based feedback control on treatment reliability, ablation volumes and rates, as well as Dice coefficients for measured versus targeted ablation zones, were statistically compared for controlled versus uncontrolled trials. Results confirm the utility of three-dimensional echo decorrelation imaging as a monitoring and control approach for clinical ablation of liver tumors.

Specimens of human liver tissue were obtained from organs explanted before liver transplant, from autopsy specimens, and from organs declined for transplant. All tissue acquisition processes, including consent from all living tissue donors, were performed under protocols approved by the University of Cincinnati Institutional Review Board.

Human liver tissue samples 24 were cut to approximately 60×60×60 mm$^3$ and stored at −80° C. Before ex vivo ablation experiments, the tissue samples 24 were retrieved from −80° C. storage, placed in phosphate-buffered saline at 25° C. (0.01 M, pH 7.4, available from Sigma Life Science, of St. Louis, MO), and thawed for one day in a laboratory refrigerator. For ablation, tissue samples 24 were placed in a 60×60×60 mm$^3$ sample container 72 that had been 3D-printed with polylactic acid filament, with an acoustic window 76 covered by a film 78, e.g., a Tegaderm adhesive membrane 78. The sample container 72 was then filled with room-temperature phosphate-buffered saline to fill any air gaps within the tissue, and was allowed to acclimate to room temperature.

The sample container 72 containing liver tissue was placed on a 3D-printed stand 74, into which an imaging probe 14 including a matrix ultrasound array (Z6Ms transesophageal transducer, available from Siemens Medical Systems, supra) was fixed within a fitted holder to face the liver tissue through the acoustic window 76. An ablation probe 18 (RITA StarBurst XLi-enhanced device with microinfusion, AngioDynamics, Latham, NY) was then inserted into the tissue sample 24 through a probe guide 30 integrated into a 3D-printed lid 80, and deployed to a tine diameter of 20 mm. This design reproducibly placed the tip of ablation probe 30 mm from the bottom and side walls of sample container 72, centered in the azimuth and elevation directions of the acquired ultrasound image at a range of about 30 mm, with an estimated placement uncertainty of 1-2 mm.

The ablation probe 18 was connected to a clinical radiofrequency generator 16 with a saline infusion pump (RITA 1500X RF Generator and Intelliflow pump, available from AngioDynamics). A grounding pad 88, adapted from a clinical dispersive electrode (RITA Thermopads, also available from AngioDynamics,) specified for use with the same generator 16 and ablation probe 18, was placed on the sample container wall furthest from the imaging probe 14, and connected to the ground plug of the radiofrequency generator 16.

For each ablation procedure, the radiofrequency generator 16 was programmed to output 50 W. For trials controlled by the default algorithm of the radiofrequency generator 16 (referred to as "uncontrolled trials" herein to distinguish them from ablation controlled by echo decorrelation imaging), ablation proceeded until the average temperature of three integrated thermocouples exceeded the target temperature of 105° C. for a duration of 3 min. The default algorithm was designed to create an approximately spherical ablation zone 92 having a diameter of 20 mm, contained completely within the pulse-echo image volume 34. Trials controlled by echo decorrelation imaging (referred to as "controlled trials") followed the same ablation algorithm, except that ablation was automatically ceased after attainment of the echo decorrelation imaging-based stopping criterion described below.

After each ablation trial, tissue was frozen inside the same sample container 72 at −80° C. for at least 12 hours. The tissue was then retrieved, partially defrosted for removal from the sample container 72, and sectioned using a commercial meat slicer at a uniform thickness of 3-4 mm. Tissue sections 90 were manually numbered, with notation of section numbers corresponding to the upper and lower boundaries of the ablation zone 92 as well as tissue sections 90 containing the probe track 94.

Tissue sections 90 were then optically scanned at 600 dpi using the above described V550 scanner, and segmented using a custom graphical user interface programmed in MATLAB. The numbered tissue sections 90 containing the probe track 94 were registered with their known position relative to the pulse-echo image volume 34. Other tissue sections 90 were then registered according to the average slice thickness for the tissue sample 24. Because the ablation zone 92 had low water content compared to the surrounding untreated tissue, expansion of the ablation zone 92 due to freezing was assumed negligible. A three-dimensional map of the ablation zone 92 was then formed for comparison with ultrasound image data.

Throughout each ablation procedure, pulse-echo image volume data was acquired using the Z6Ms imaging probe 14 and the Acuson SC2000 ultrasound scanner 12, which provides access to beamformed, demodulated in-phase/quadrature scan lines. Pulse-echo image volumes 34 were acquired using an imaging frequency of 4.5 MHz and a depth of 70 mm, with 85×67 in-phase/quadrature scan lines recorded at a sampling rate of 5.0 MHz, spanning 90°×90° in the azimuth and elevation directions, respectively. In this configuration, the frame rate was 20 volumes per second. Pairs of sequential pulse-echo image volumes 34 separated by an inter-frame time τ=50 ms were acquired and transferred a computer running a custom MATLAB program configured to generate echo decorrelation image volumes. Due to time requirements for data storage and transfer, the paired pulse-echo image volumes were acquired at 22 second intervals throughout ablation.

For computation of echo decorrelation image volumes, in-phase/quadrature pulse-echo image volumes were scan-converted to a Cartesian grid spanning 60×60×60 mm$^3$ with an isotropic step size of 0.5 mm in each direction. The three-dimensional echo decorrelation image volumes were then generated from the converted pulse-echo image volumes. Scan conversion from frustum coordinates (r, θ, φ) to Cartesian coordinates (x, y, z) was performed using the relationships defined by Equations 1-3.

Echo decorrelation per unit time between sequential complex pulse-echo image volumes $I_0$ and $I_1$ was computed using Equation 28, where r is the position within the pulse-echo image volume, n is the index of the present pulse-echo image volume pair, and the inter-frame time τ=50 ms. The above use of Equation 28 incorporates a zero-lag (τ=0), spatially windowed cross-correlation between the pulse-echo image volumes, $$R_{01}(r,n) = \langle I_0(r,n)^* I_1(r,n) \rangle \qquad \text{Eqn. 31}$$

where angle brackets denote convolution with a three-dimensional Gaussian window with width parameter σ=3 mm, and $I_0(r,n)^*$ is the complex conjugate of the pulse-echo image volume $I_0$. Also incorporated the above expression is the product of zero-lag, spatially windowed autocorrelations of the two pulse-echo image volumes $\beta^2(r,n)$, as defined by Equation 25. It may be recalled that the autocorrelations $R_{00}$ and $R_{11}$ are defined analogously to $R_{01}$. Equation 31 incorporates normalization by a combination of the local autocorrelation product $\beta^2(r,n)$ and its spatial mean $\overline{\beta^2}(n)$ to minimize spuriously large decorrelation in regions of high and low echogenicity. The resulting echo decorrelation image volume Δ(r,n) is zero at positions where no differences occurred between the sequential pulse-echo image volumes $I_0$ and $I_1$, and is largest where local echo changes are greatest. In order to incorporate all substantial measured echo changes, cumulative echo decorrelation may be defined as the temporal maximum decorrelation of Δ(r,n) at each position r, over all times since the beginning of ablation.

Figure 14:
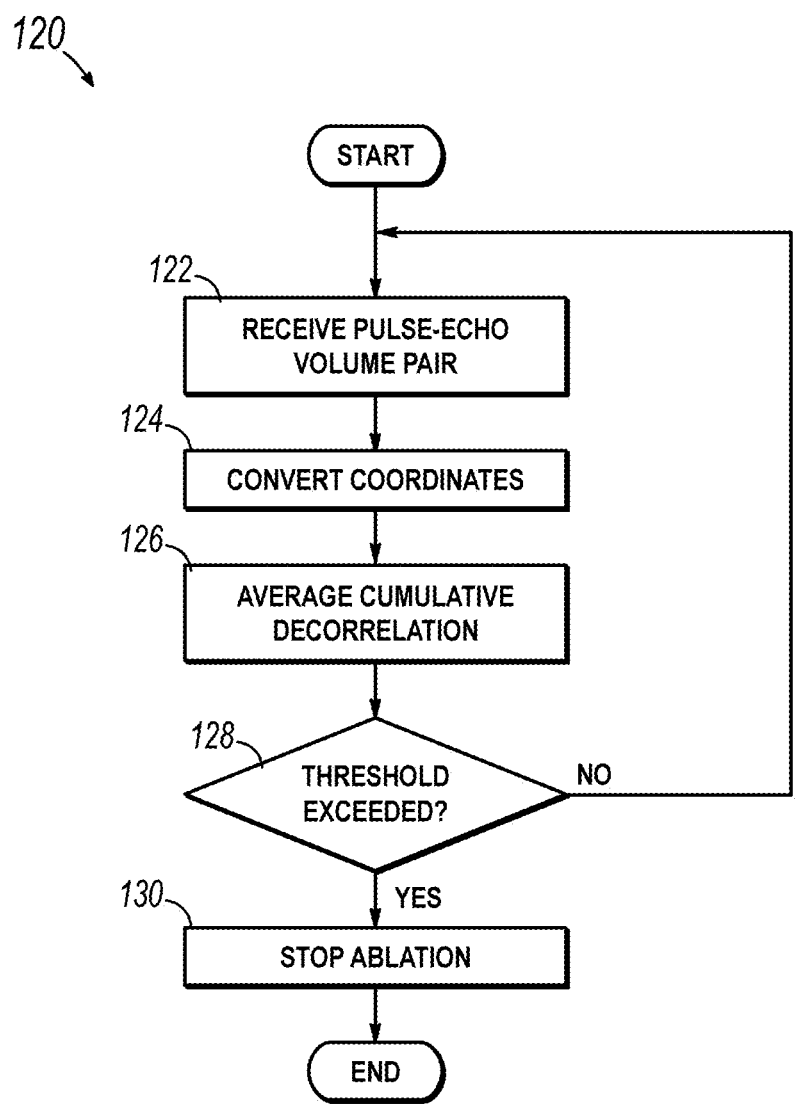
FIG. 14 is a flowchart of another process for controlling an ablation that may be performed by the ablation system of FIG. 1.

FIG. 14 depicts a flowchart of a process 120 that may be implemented by one or more of the ultrasound scanner 12, system controller 20, or another suitable computing device. In block 122, the process 120 receives a pulse-echo image volume pair, e.g., from the ultrasound scanner 12. In response to receiving the pulse-echo image volume pair, the process 120 may proceed to block 124 and convert the pulse-echo image volume data from one coordinate system (e.g., pyramidal coordinates (r, θ, φ)) into another coordinate system (e.g., Cartesian coordinates (x, y, z)). The process 120 may then proceed to block 126 calculate the average cumulative decorrelation in the region of interest 26, e.g., a spherical region of interest 26 having a radius of 10 mm for the below experimental data. In block 128, the process 120 determines if the echo decorrelation parameter has exceeded a predetermined threshold. If the echo decorrelation parameter has not exceeded the predetermined threshold ("NO" branch of decision block 128), the process 120 may return to block 122 and continue receiving pulse-echo image volume pairs. If the control parameter has exceeded the predetermined threshold ("YES" branch of decision block 128), the process 120 may proceed to block 130 and stop the ablation, e.g., by shutting of the radiofrequency generator 16. The process 120 may also cause the ultrasound scanner 12 to stop generating pulse-echo image volumes 34.

Experimental data was generated using a cumulative echo decorrelation averaged within a 20 mm diameter spherical region of interest 26 centered at the tip 28 of ablation probe 18, which is a region corresponding to the expected ablation zone 92. For controlled trials, after each data acquisition, the average cumulative echo decorrelation $\hat{\Delta}_{cum}$ within this control region of interest 26 was compared to a predefined threshold. When this threshold was surpassed, the system controller ended the ablation by reducing the output of the radiofrequency generator 16 to zero.

In order to determine a suitable echo decorrelation threshold for real-time control, preliminary ablation trials were performed, including six uncontrolled trials (N=3 normal liver, N=1 fatty liver, and N=2 cirrhotic liver specimens), and five controlled ablation trials with varying thresholds ($\log_{10}[\hat{\Delta}_{cum}/\text{ms}]$) between −2.6 and −2.3 (N=1 normal liver, N=4 cirrhotic liver specimens). Final average cumulative decorrelation within the 20 mm control region of interest 26 was found to be −2.62±0.38 (mean±standard deviation $\log_{10}[\hat{\Delta}_{cum}/\text{ms}]$) for eleven preliminary trials, and exceeded −2.8 in three of five preliminary controlled trials. Based on these results, a predefined threshold of −2.8 ($\log_{10}[\hat{\Delta}_{cum}/\text{ms}]$) was chosen.

Using this predefined threshold, six controlled trials were performed. Five of these trials (N=4 normal liver, 1 fatty liver) attained the specified control threshold for Lim and were thus considered successfully controlled. Ablation and imaging outcomes were compared between this group of five successfully controlled trials and the prior group of six uncontrolled trials.

To assess differences in ablation outcomes between the successfully controlled and uncontrolled groups, ablated volumes were defined as the summed volume of all segmented voxels which were ablated in each trial. Ablation rates were then computed as the ratio between ablation volume and the duration of radiofrequency ablation for each trial.

To assess conformity with the planned ablation zone 92, Dice coefficients were computed between the segmented ablation zone 92 and the targeted ablation zone 92, i.e., a sphere having a diameter of 20 mm centered at the tip 28 of ablation probe 18. For this analysis, the Dice coefficient was defined as:

$$\text{Dice} = 2(P \cap S)/(P+S) \qquad \text{Eqn. 32}$$

where P denotes the planned ablation volume, S denotes the segmented ablation volume, and (P∩S) denotes the volume of the intersection of P and S, i.e., the total volume of successfully ablated voxels within the originally planned ablation zone 92.

To assess local prediction of thermal ablation, three-dimensional echo decorrelation image volumes were compared with ablated tissue histology using receiver operating characteristic curve analysis. Segmented three-dimensional ablated and unablated regions in controlled and uncontrolled trials were compared voxel-by-voxel with measured echo decorrelation within a spherical region of interest 26 having a 40 mm diameter centered on the tip 28 of ablation probe 18. Assessment of statistical significance for receiver operating characteristics curves accounted for the effective number of independent predictions associated with the finite window width σ.

All ablation outcome metrics were found to be normally distributed by the Shapiro-Wilk test (p>0.05), and were thus compared by Student t tests. Ablated volumes averaged 4.5 ml and 4.9 ml for controlled and uncontrolled trials, respectively, and were not significantly different (p>0.05). Ablation rates were 1.09 ml/min and 0.81 ml/min for controlled and uncontrolled trials, respectively, which is considered to be a marginal difference (p=0.063).

Dice coefficients between the segmented and targeted ablation zones were 0.61 and 0.66 for controlled and uncontrolled trials, respectively, and were not significantly different. AUC for ablation prediction was 0.86 for controlled and 0.88 for uncontrolled trials, thus not significantly different. Dice coefficient and AUC values were likely affected by the finite tissue section thickness (3-4 mm), resulting in lower resolution of the segmented ablation zone in the elevation direction.

The above results show that radiofrequency ablation of human liver tissue can be successfully controlled by three-dimensional echo decorrelation imaging, even with substantial time between echo decorrelation image volumes, e.g., 22 seconds. Consistent with the data from bovine livers, the results suggest control using echo decorrelation imaging can increase the ablation rate. High AUC values for both controlled and uncontrolled trials indicate success in local ablation prediction, despite relatively low temporal resolution of the echo decorrelation imaging.

More frequent echo decorrelation image volume acquisition during ablation may provide more information on heat-induced tissue changes throughout the ablation process, enabling more precise control. One approach for increasing the rate of data acquisition would be bi-plane imaging, i.e., acquisition of echo data only in the two parallel planes, e.g., the x=0 plane, and the y=0 plane. Another way for increasing the rate of data acquisition would be to implement the control processes on internal clinical scanner software. The method's high computational efficiency could thereby enable real-time three-dimensional echo decorrelation imaging to be computed and displayed in a manner similar to power Doppler imaging.

For clinical implementation using the above described control approaches, it may be advantageous to compensate for motion-induced echo decorrelation. One approach may measure echo decorrelation prior to ablation, then compensate total measured decorrelation to remove motion effects based on a theoretical model for motion-induced and heat-induced decorrelation. Methods of compensating for motion-induced decorrelation are described in more detail below.

EXPERIMENTAL RESULTS—EX VIVO CARDIAC ABLATION

As described above, echo decorrelation imaging may be susceptible to artifacts caused by motion, e.g., motion due to the cardiac cycle or patient respiration. A method of compensating for artifactual decorrelation in echo decorrelation images caused by motion in ex vivo ablation of bovine cardiac muscle is described below. The below experimental data was obtained using a Stockert 70 radiofrequency generator 16 and a 4-mm Celsius ablation probe 18 including a Z6Ms transesophageal transducer, both of which are available from Biosense Webster, Inc. of Irvine CA. An ablation duration of three minutes at the target ablation temperature of 90° C. was used to generate thermal lesions having a diameter of about 10 mm. Cyclical motion was induced into the tissue sample 24 by a stepping motor system with velocities up to 10 mm/second and a travel range of 15 mm. Pulse-echo image volumes 34 were acquired using the above described Acuson SC2000 ultrasound scanner 12 and an imaging probe 14.

Throughout ablation, at intervals of 5-6 seconds, sequentially paired bi-plane images were acquired as complex beamformed pulse-echo image volumes 34 with an inter-frame time τ of 9-13 ms. Regions of interest 26 included an ablation region of interest centered on the tip 28 of ablation probe 18 (e.g., an intracardiac catheter) and a reference region of interest outside the ablation zone 92. These regions of interest 26 were tracked using detection of the myocardial wall boundary and spatial cross-correlation. An artifactual decorrelation component of an echo decorrelation image volume including the ablation region of interest was compensated for based on motion-induced decorrelation measured in the reference region of interest. Receiver operating characteristic curves were used to characterize accuracy for predictions of local myocardial ablation by motion-compensated echo decorrelation imaging as a function of the induced motion amplitude.

Thermal ablation of the myocardium may be performed by intracardiac catheter to form deep lesions in the myocardium, thereby blocking irregular electrical signals and restoring typical cardiac rhythms. Typical ablation sites may include ventricular, supraventricular, and atrioventricular nodes. Navigation guidance may be provided by fluoroscopy, electromagnetic sensors, etc. Feedback may include temperature and electrical impedance sensors on the catheter.

Echo decorrelation artifacts may be caused by tissue motion and electronic noise. For example, cardiac motion may have a peak velocity of about 60 mm/second during the systolic portion of the cardiac cycle, and 0-20 mm/second during the diastolic portion of the cardiac cycle. Motion-induced artifacts in the echo decorrelation image volume were determined by measuring the maximum decorrelation $\Delta_M$ of a selected area (e.g., a 4.6×4.6 mm$^2$ area) in the reference region of interest, e.g., about 13 mm from the tip 28 of the ablation probe 18. Motion effects where then compensated for in the echo decorrelation image volume using Equations 20 and 21 as described above.

Decorrelation was computed and accumulated within the reference region of interest 26, and the surface of the moving tissue found by grayscale thresholding. Displacement between pulse-echo image volume pairs was determined using a two-dimensional cross-correlation of in-phase/quadrature echo data within a 27×27 mm$^2$ region centered on the array axis 36 at the moving tissue surface. The region of interest for decorrelation computation had an azimuthal width of 30.8 mm centered at the tip 28 of ablation probe 18, and a depth from the moving tissue surface to about 12.3 mm beyond the tip 28 of ablation probe 18.

Tissue was partially sectioned along the azimuthal plane (x=0) and elevation plane (y=0). Tissue samples were stained by applying a one percent 2,3,5-triphenyltetrazolium chloride (TTC) solution for 40 minutes, the tissue planes optically scanned at 1200 dpi, and the resulting images cropped to match the width of the decorrelation region of interest. The ablation zone 92 was segmented manually based on TTC uptake, the segmented tissue map scaled to match the ultrasound image, and translated/rotated to register versus the edge of the tissue sample. Receiver operating characteristics curves were then computed to predict the local ablation from the decorrelation. The cumulative decorrelation was superimposed on corresponding bi-plane B-scans, and the echo decorrelation displayed over a range of −5 to −1 ($\log_{10} \Delta$/ms).

Figure 15:
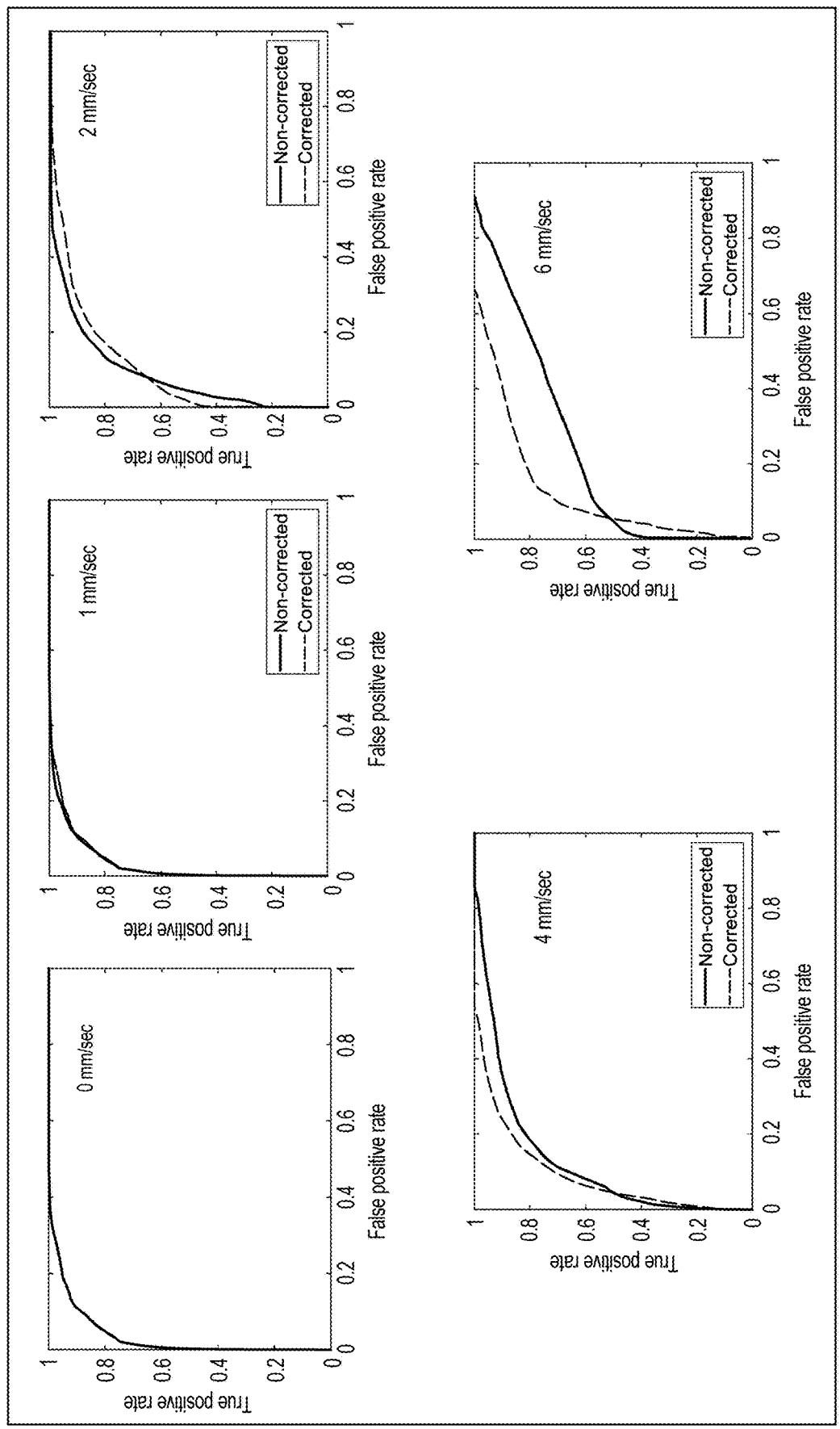
FIG. 15 is a graphical view of true positive rate versus false positive rate for echo decorrelation imaging based control systems with and without compensation for movement of the tissue sample.

FIG. 15 depicts graphs of the true positive rate versus false positive rate for the above data for no motion, and for motions of 1 mm/sec, 2 mm/sec, 4 mm/sec, and 6 mm/sec. As can be seen from the graphs, motion compensation applied according to Equations 20 and 21 had little effect at 1 mm/sec, and a slight adverse effect at 2 mm/sec. However, the improvement in the true positive to false positive ratio is significant at 4 mm/sec and 6 mm/sec. Table III shows the AUC and Optimal Cutoff values for each scenario plotted in FIG. 15, showing AUC values as higher with compensation than without compensation at 4 mm/sec and 6 mm/sec.

TABLE III

| Velocity | AUC | Optimal Cutoff |
| --- | --- | --- |
| 0 mm/sec - no compensation | 0.9687 | −4.18 |
| 1 mm/sec - no compensation | 0.9687 | −3.11 |
| 1 mm/sec - with compensation | 0.9660 | −3.49 |
| 2 mm/sec - no compensation | 0.9153 | −2.80 |
| 2 mm/sec - with compensation | 0.9036 | −3.93 |
| 4 mm/sec - no compensation | 0.8779 | −2.25 |
| 4 mm/sec - with compensation | 0.9111 | −2.85 |
| 6 mm/sec - no compensation | 0.7732 | −2.16 |
| 6 mm/sec - with compensation | 0.8807 | −3.86 |

The above results demonstrate that echo decorrelation successfully predicts local ablation of myocardium ex vivo, that tissue motion can be tracked using cross-correlation, and that compensating for motion-induced echo decorrelation significantly improves echo decorrelation image volumes. Motion-compensated echo decorrelation imaging effectively predicts local ablation up to at least velocities 6 mm/sec, however, no upper velocity bound for motion compensation was determined. Applying echo decorrelation imaging to improve ablation in vivo application may benefit from gating to the motion being compensated for, e.g., the cardiac cycle.

Figure 16:
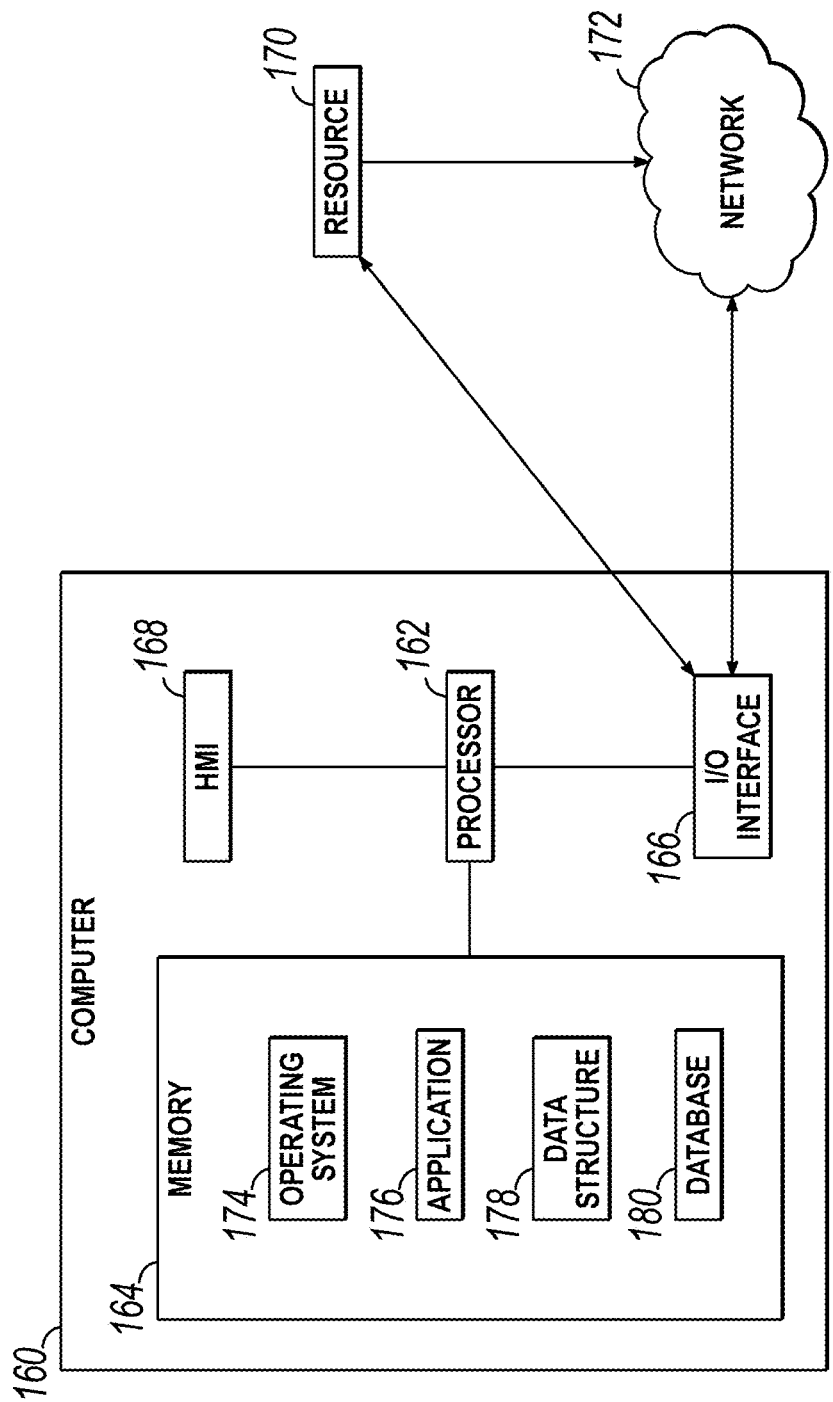
FIG. 16 is a diagrammatic view of a computer that may be used to implement one or more of the components or processes shown in FIGS. 1-15.

Referring now to FIG. 16, embodiments of the invention described above, or portions thereof, may be implemented using one or more computer devices or systems, such as exemplary computer 160. The computer 160 may include a processor 162, a memory 164, an input/output (I/O) interface 166, and a Human Machine Interface (HMI) 168. The computer 160 may also be operatively coupled to one or more external resources 170 via a network 172 or I/O interface 166. External resources may include, but are not limited to, servers, databases, mass storage devices, peripheral devices, cloud-based network services, or any other resource that may be used by the computer 160.

The processor 162 may operate under the control of an operating system 174 that resides in memory 164. The operating system 174 may manage computer resources so that computer program code embodied as one or more computer software applications, such as an application 176 residing in memory 164, may have instructions executed by the processor 162. In an alternative embodiment, the processor 162 may execute the application 176 directly, in which case the operating system 174 may be omitted. One or more data structures 178 may also reside in memory 164, and may be used by the processor 162, operating system 174, or application 176 to store or manipulate data.

The I/O interface 166 may provide a machine interface that operatively couples the processor 162 to other devices and systems, such as the external resource 160 or the network 172. The application 176 may thereby work cooperatively with the external resource 160 or network 172 by communicating via the I/O interface 166 to provide the various features, functions, applications, processes, or modules comprising embodiments of the invention. The application 176 may also have program code that is executed by one or more external resources 170, or otherwise rely on functions or signals provided by other system or network components external to the computer 160. Indeed, given the nearly endless hardware and software configurations possible, persons having ordinary skill in the art will understand that embodiments of the invention may include applications that are located externally to the computer 160, distributed among multiple computers or other external resources 170, or provided by computing resources (hardware and software) that are provided as a service over the network 172, such as a cloud computing service.

The HMI 168 may be operatively coupled to the processor 162 of computer 160 to allow a user to interact directly with the computer 160. The HMI 168 may include video or alphanumeric displays, a touch screen, a speaker, and any other suitable audio and visual indicators capable of providing data to the user. The HMI 168 may also include input devices and controls such as an alphanumeric keyboard, a pointing device, keypads, pushbuttons, control knobs, microphones, etc., capable of accepting commands or input from the user and transmitting the entered input to the processor 162.

A database 180 may reside in memory 164, and may be used to collect and organize data used by the various systems and modules described herein. The database 180 may include data and supporting data structures that store and organize the data. In particular, the database 180 may be arranged with any database organization or structure including, but not limited to, a relational database, a hierarchical database, a network database, or combinations thereof. A database management system in the form of a computer software application executing as instructions on the processor 162 may be used to access the information or data stored in records of the database 180 in response to a query, which may be dynamically determined and executed by the operating system 174, other applications 166, or one or more modules.

In general, the routines executed to implement the embodiments of the invention, whether implemented as part of an operating system or a specific application, component, program, object, module or sequence of instructions, or a subset thereof, may be referred to herein as "program code." Program code typically comprises computer-readable instructions that are resident at various times in various memory and storage devices in a computer and that, when read and executed by one or more processors in a computer, cause that computer to perform the operations necessary to execute operations or elements embodying the various aspects of the embodiments of the invention. Computer-readable program instructions for carrying out operations of the embodiments of the invention may be, for example, assembly language, source code, or object code written in any combination of one or more programming languages.

The program code embodied in any of the applications/modules described herein is capable of being individually or collectively distributed as a computer program product in a variety of different forms. In particular, the program code may be distributed using a computer-readable storage medium having computer-readable program instructions thereon for causing a processor to carry out aspects of the embodiments of the invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, or operations specified in the text of the specification, the flowcharts, sequence diagrams, or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, or operations specified in the text of the specification, flowcharts, sequence diagrams, or block diagrams.

The flowcharts and block diagrams depicted in the figures illustrate the architecture, functionality, or operation of possible implementations of systems, methods, or computer program products according to various embodiments of the invention. In this regard, each block in the flowchart or block diagrams may represent a module, segment, or portion of instructions, which comprises one or more executable instructions for implementing the specified logical function or functions.

In certain alternative embodiments, the functions, acts, or operations specified in the text of the specification, the flowcharts, sequence diagrams, or block diagrams may be re-ordered, processed serially, or processed concurrently consistent with embodiments of the invention. Moreover, any of the flowcharts, sequence diagrams, or block diagrams may include more or fewer blocks than those illustrated consistent with embodiments of the invention. It should also be understood that each block of the block diagrams or flowcharts, or any combination of blocks in the block diagrams or flowcharts, may be implemented by a special purpose hardware-based system configured to perform the specified functions or acts, or carried out by a combination of special purpose hardware and computer instructions.

The terminology used herein is for the purpose of describing particular embodiments only and is not intended to be limiting of the embodiments of the invention. As used herein, the singular forms "a", "an" and "the" are intended to include both the singular and plural forms, and the terms "and" and "or" are each intended to include both alternative and conjunctive combinations, unless the context clearly indicates otherwise. It will be further understood that the terms "comprises" or "comprising," when used in this specification, specify the presence of stated features, integers, actions, steps, operations, elements, or components, but do not preclude the presence or addition of one or more other features, integers, actions, steps, operations, elements, components, or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A method of controlling an ablation process, comprising:
    receiving a plurality of pulse-echo image volumes each captured during ablation and including a region of interest;
    defining a first pulse-echo image volume pair that includes a first pulse-echo image volume of the plurality of pulse-echo image volumes and a second pulse-echo image volume of the plurality of pulse-echo image volumes;
    generating an echo decorrelation image volume from the first pulse-echo image volume pair;
    deriving a control parameter from the echo decorrelation image volume by:
        compensating for an artifactual decorrelation component of the echo decorrelation image volume to generate a corrected echo decorrelation image volume by:
            defining a second pulse-echo image volume pair that includes a third pulse-echo image volume of the plurality of pulse-echo image volumes and a fourth pulse-echo image volume of the plurality of pulse-echo image volumes,
            generating a compensation echo decorrelation image volume from the second pulse-echo image volume pair,
            defining the corrected echo decorrelation image volume including a plurality of corrected echo decorrelation image voxels by, for each echo decorrelation image voxel of the echo decorrelation image volume:
                subtracting an echo decorrelation value of a respective compensation echo decorrelation image voxel of the compensation echo decorrelation image volume from the echo decorrelation value of the echo decorrelation image voxel of the echo decorrelation image volume to define a difference value,
                subtracting the echo decorrelation value of the respective compensation echo decorrelation image voxel of the compensation echo decorrelation image volume from unity to define a normalization value, and
                dividing the difference value by the normalization value to generate a corrected echo decorrelation value of a respective corrected echo decorrelation image voxel, and
        deriving the control parameter from the corrected echo decorrelation image volume; and
    adjusting an amount of power provided to an ablation probe located in the region of interest based on the control parameter.

2. The method of claim 1, wherein adjusting the amount of power provided to the ablation probe based on the control parameter includes:
    comparing the control parameter to a predetermined threshold; and
    reducing the amount of power provided to the ablation probe in response to the control parameter exceeding the predetermined threshold.

3. The method of claim 1, wherein each pulse-echo image volume of the plurality of pulse-echo image volumes includes a plurality of pulse-echo image voxels each having a position within the respective pulse-echo image volume, the echo decorrelation image volume includes a plurality of echo decorrelation image voxels each associated with a respective pulse-echo image voxel of the plurality of pulse-echo image voxels, and the control parameter is a spatial mean of each echo decorrelation image voxel within the region of interest.

4. The method of claim 1, wherein each pulse-echo image volume of the plurality of pulse-echo image volumes includes a plurality of pulse-echo image voxels each having a position within the respective pulse-echo image volume, the echo decorrelation image volume includes a plurality of echo decorrelation image voxels each associated with a respective pulse-echo image voxel of the plurality of pulse-echo image voxels, and the control parameter is a minimum echo decorrelation value of the echo decorrelation image voxels within the region of interest.

5. The method of claim 1, wherein each pulse-echo image volume of the plurality of pulse-echo image volumes includes a plurality of pulse-echo image voxels each having a position within the respective pulse-echo image volume, the echo decorrelation image volume includes a plurality of echo decorrelation image voxels each associated with a respective pulse-echo image voxel of the plurality of pulse-echo image voxels, and generating the corrected echo decorrelation image volume further includes:
  calculating a motion-induced decorrelation value produced by a movement in a reference region of interest,
  wherein, for each echo decorrelation image voxel of the echo decorrelation image volume, the echo decorrelation value of the respective compensation echo decorrelation image voxel of the compensation echo decorrelation image volume is equal to the motion-induced decorrelation value.

6. The method of claim 5, wherein calculating the motion-induced decorrelation value produced by the movement in the reference region of interest includes measuring a maximum decorrelation of a selected area in the reference region of interest.

7. The method of claim 1, further comprising:
  defining a globally normalized echo decorrelation normalized by a spatial mean of an autocorrelation product within the region of interest.

8. The method of claim 1, further comprising:
  predicting ablation zone margins and volumes using weighted K-means clustering.

9. A system for controlling an ablation process, comprising:
  one or more processors; and
  a memory coupled to the one or more processors and including program code that, when executed by the one or more processors, causes the system to:
  receive a plurality of pulse-echo image volumes each captured during ablation and including a region of interest;
  define a first pulse-echo image volume pair that includes a first pulse-echo image volume of the plurality of pulse-echo image volumes and a second pulse-echo image volume of the plurality of pulse-echo image volumes;
  generate an echo decorrelation image volume from the first pulse-echo image volume pair;
  derive a control parameter from the echo decorrelation image volume by:
    compensating for an artifactual decorrelation component of the echo decorrelation image volume to generate a corrected echo decorrelation image volume by:
      defining a second pulse-echo image volume pair that includes a third pulse-echo image volume of the plurality of pulse-echo image volumes and a fourth pulse-echo image volume of the plurality of pulse-echo image volumes,
      generating a compensation echo decorrelation image volume from the second pulse-echo image volume pair,
      defining the corrected echo decorrelation image volume including a plurality of corrected echo decorrelation image voxels by, for each echo decorrelation image voxel of the echo decorrelation image volume:
        subtracting an echo decorrelation value of a respective compensation echo decorrelation image voxel of the compensation echo decorrelation image volume from the echo decorrelation value of the echo decorrelation image voxel of the echo decorrelation image volume to define a difference value,
        subtracting the echo decorrelation value of the respective compensation echo decorrelation image voxel of the compensation echo decorrelation image volume from unity to define a normalization value, and
        dividing the difference value by the normalization value to generate a corrected echo decorrelation value of a respective corrected echo decorrelation image voxel, and
      deriving the control parameter from the corrected echo decorrelation image volume; and
  adjust an amount of power provided to an ablation probe located in the region of interest based on the control parameter.

10. The system of claim 9, wherein the program code causes the system to adjust the amount of power provided to the ablation probe based on the control parameter by causing the system to:
  compare the control parameter to a predetermined threshold; and
  reduce the amount of power provided to the ablation probe in response to the control parameter exceeding the predetermined threshold.

11. The system of claim 9, wherein:
  each pulse-echo image volume of the plurality of pulse-echo image volumes includes a plurality of pulse-echo image voxels each having a position within the respective pulse-echo image volume,
  the echo decorrelation image volume includes a plurality of echo decorrelation image voxels each associated with a respective pulse-echo image voxel of the plurality of pulse-echo image voxels, and
  the control parameter is one of a spatial mean of each echo decorrelation image voxel within the region of interest or a minimum echo decorrelation value of the echo decorrelation image voxels within the region of interest.

12. The system of claim 9, wherein:
  each pulse-echo image volume of the plurality of pulse-echo image volumes includes a plurality of pulse-echo image voxels each having a position within the respective pulse-echo image volume,
  the echo decorrelation image volume includes a plurality of echo decorrelation image voxels each associated with a respective pulse-echo image voxel of the plurality of pulse-echo image voxels, and
  the program code causes the system to generate the corrected echo decorrelation image volume by causing the system to further:

calculate a motion-induced decorrelation value produced by a movement in a reference region of interest, wherein, for each echo decorrelation image voxel of the echo decorrelation image volume, the echo decorrelation value of the respective compensation echo decorrelation image voxel of the compensation echo decorrelation image volume is equal to the motion-induced decorrelation value.

13. The system of claim 12, wherein the program code causes the system to calculate the motion-induced decorrelation value produced by the movement in the reference region of interest by causing the system to measure a maximum decorrelation of a selected area in the reference region of interest.

14. The system of claim 9, wherein the program code further causes the system to:
define a globally normalized echo decorrelation normalized by a spatial mean of an autocorrelation product within the region of interest.

15. The system of claim 9, wherein the program code further causes the system to:
predict ablation zone margins and volumes using weighted K-means clustering.

16. A computer program product for controlling an ablation process, comprising:
a non-transitory computer-readable storage medium; and
program code stored on the non-transitory computer-readable storage medium that, when executed by one or more processors, causes the one or more processors to:
receive a plurality of pulse-echo image volumes each captured during ablation and including a region of interest;
define a first pulse-echo image volume pair that includes a first pulse-echo image volume of the plurality of pulse-echo image volumes and a second pulse-echo image volume of the plurality of pulse-echo image volumes;
generate an echo decorrelation image volume from the first pulse-echo image volume pair;
derive a control parameter from the echo decorrelation image volume by:
compensating for an artifactual decorrelation component of the echo decorrelation image volume to generate a corrected echo decorrelation image volume by:
defining a second pulse-echo image volume pair that includes a third pulse-echo image volume of the plurality of pulse-echo image volumes and a fourth pulse-echo image volume of the plurality of pulse-echo image volumes,
generating a compensation echo decorrelation image volume from the second pulse-echo image volume pair,
defining the corrected echo decorrelation image volume including a plurality of corrected echo decorrelation image voxels by, for each echo decorrelation image voxel of the echo decorrelation image volume:
subtracting an echo decorrelation value of a respective compensation echo decorrelation image voxel of the compensation echo decorrelation image volume from the echo decorrelation value of the echo decorrelation image voxel of the echo decorrelation image volume to define a difference value,
subtracting the echo decorrelation value of the respective compensation echo decorrelation image voxel of the compensation echo decorrelation image volume from unity to define a normalization value, and
dividing the difference value by the normalization value to generate a corrected echo decorrelation value of a respective corrected echo decorrelation image voxel, and
deriving the control parameter from the corrected echo decorrelation image volume; and
adjust an amount of power provided to an ablation probe located in the region of interest based on the control parameter.

17. The program product of claim 16, wherein the program code further causes the one or more processors to:
define a globally normalized echo decorrelation normalized by a spatial mean of an autocorrelation product within the region of interest.

18. The program product of claim 16, wherein the program code further causes the one or more processors to:
predict ablation zone margins and volumes using weighted K-means clustering.

* * * * *